US008106004B2

(12) United States Patent
Hendrix et al.

(10) Patent No.: US 8,106,004 B2
(45) Date of Patent: Jan. 31, 2012

(54) METHODS OF INHIBITING TUMOR CELL AGGRESSIVENESS USING THE MICROENVIRONMENT OF HUMAN EMBRYONIC STEM CELLS

(75) Inventors: Mary Jessica Hendrix, Evanston, IL (US); Lynne-Marie Postovit, London (CA); Richard Edward Barnet Seftor, Chicago, IL (US); Elisabeth Ann Seftor, Chicago, IL (US)

(73) Assignee: Children's Memorial Hospital, Chicago, IL (US)

( * ) Notice: Subject to any disclaimer, the term of this patent is extended or adjusted under 35 U.S.C. 154(b) by 37 days.

(21) Appl. No.: 12/045,134

(22) Filed: Mar. 10, 2008

(65) Prior Publication Data
US 2009/0186801 A1 Jul. 23, 2009

Related U.S. Application Data

(63) Continuation-in-part of application No. 11/829,070, filed on Jul. 26, 2007, now Pat. No. 7,666,423.

(60) Provisional application No. 60/820,740, filed on Jul. 28, 2006, provisional application No. 60/941,343, filed on Jun. 1, 2007.

(51) Int. Cl.
*A01N 37/18* (2006.01)
*C07H 1/00* (2006.01)
*C12N 5/00* (2006.01)
(52) U.S. Cl. .............................. 514/2; 530/350; 435/325
(58) Field of Classification Search ...... 514/2; 530/350; 435/325
See application file for complete search history.

(56) References Cited

U.S. PATENT DOCUMENTS

| | | | |
|---|---|---|---|
| 5,916,751 A | 6/1999 | Tabibzadeh et al. | |
| 6,027,917 A | 2/2000 | Celeste et al. | |
| 6,294,330 B1 | 9/2001 | Michnick et al. | |
| 6,428,966 B1 | 8/2002 | Lee et al. | |
| 6,472,179 B2 | 10/2002 | Stahl et al. | |
| 6,635,480 B1 | 10/2003 | Lee et al. | |
| 6,649,588 B1 | 11/2003 | Tabibzadeh et al. | |
| 6,747,004 B1 | 6/2004 | Tabibzadeh | |
| 6,878,807 B2 | 4/2005 | Desnoyers et al. | |
| 7,074,592 B2 | 7/2006 | Ashkenazi et al. | |
| 7,151,086 B2 | 12/2006 | Celeste et al. | |
| 7,211,644 B1 | 5/2007 | Tabibzadeh | |
| 7,270,963 B2 | 9/2007 | Lee et al. | |
| 7,307,152 B2 | 12/2007 | Desnoyers et al. | |
| 6,492,493 B2 | 4/2008 | Celeste et al. | |
| 7,147,853 B2 | 4/2008 | Goddard et al. | |
| 7,666,423 B2 | 2/2010 | Hendrix et al. | |
| 2002/0086351 A1 | 7/2002 | Ebner et al. | |
| 2003/0021792 A1 | 1/2003 | Roben et al. | |
| 2003/0069408 A1 | 4/2003 | Ebner et al. | |
| 2003/0224411 A1 | 12/2003 | Stanton et al. | |
| 2004/0147045 A1 | 7/2004 | Nelson | |
| 2004/0152885 A1 | 8/2004 | Amegadzie et al. | |
| 2004/0180347 A1 | 9/2004 | Stanton et al. | |
| 2004/0214324 A1 | 10/2004 | Isacson et al. | |
| 2005/0144660 A1 | 6/2005 | Mishra | |
| 2005/0208045 A1 | 9/2005 | Vale et al. | |
| 2006/0099576 A1 | 5/2006 | Tabibzadeh | |
| 2006/0134636 A1 | 6/2006 | Stanton et al. | |
| 2007/0010012 A1 | 1/2007 | Gold et al. | |
| 2007/0031823 A1 | 2/2007 | Bentwich | |
| 2007/0042958 A1 | 2/2007 | Knopf et al. | |
| 2007/0065415 A1 | 3/2007 | Kleinsek et al. | |
| 2007/0077553 A1 | 4/2007 | Bentwich | |
| 2007/0078101 A1 | 4/2007 | Brivanlou et al. | |
| 2007/0105122 A1 | 5/2007 | Ota et al. | |
| 2007/0155661 A1 | 7/2007 | Kim | |
| 2007/0281355 A1 | 12/2007 | Dalton et al. | |
| 2010/0105610 A1 | 4/2010 | Hendrix et al. | |
| 2010/0273707 A1 | 10/2010 | Hendrix et al. | |

FOREIGN PATENT DOCUMENTS
WO WO-2008/014426 A2 1/2008

OTHER PUBLICATIONS

Hamman et al., 2005, Biodrugs, vol. 19, No. 3, p. 165-177.*
Torchilin et al., 2003. DDT, vol. 8, No. 6, p. 259-266.*
Skolnick et al., 2000, Trends in Biotech, vol. 18, p. 34-39.*
Tomasinsig et al., 2005, Current Protein and Peptide Science, vol. 6, p. 23-34.*
Smallwood et al., 2002 Virology, vol. 304, p. 135-145.*
Chattopadhyay et al., 2004, Virus Research, vol. 99, p. 139-145.*
Postovit Lynne-Marie et al.: "A three-dimensional model to study the epigenetic effects induced by he microenvironment of human embryonic stem cells," Stem Cells (Miamisburg), vol. 24, No. 3, Mar. 2006, pp. 501-505.
Minchiotti Gabriella: "Nodal-dependant Cripto signaling in ES cells: from stem cells to tumor biology," Oncogene, vol. 24, No. 37, Aug. 2005, pp. 5668-5675.
Lee Lisa M.J. et al.: "The fate of human malignant melanoma cells transplanted into zebrafish embryos: Assessment of migration and cell division in the absence of tumor formation," Developmental Dynamics, vol. 233, No. 4, Aug. 2005, pp. 1560-1570.
Kulesa Paul M. et al.: "Reprogramming metastatic melanoma cells to assume a neural crest cell-like phenotype in an embryonic microenvironment," Proceedings of the National Academy of Sciences of the United States of America, vol. 103, No. 10, Mar. 2006, pp. 3752-3757.

(Continued)

*Primary Examiner* — Shin-Lin Chen
(74) *Attorney, Agent, or Firm* — Patton Boggs LLP

(57) ABSTRACT

The invention provides compositions comprising one or more isolated factors from a microenvironment of human embryonic stem cells (hESCs), including, but not limited to, Lefty and inhibitors of Nodal. The invention also provides methods of utilizing factors derived from human embryonic stem cells (hESC) and their microenvironment to treat and prevent tumor formation and progression and to inhibit tumor cell aggressiveness. The invention further provides methods of inhibiting tumor cell growth and/or treating aggressive tumors in a mammal comprising administering to the mammal, having at least one tumor cell present in its body, an effective amount of an inhibitor of Nodal activity.

5 Claims, 21 Drawing Sheets

OTHER PUBLICATIONS

Topczewska Jolanta M. et al.: "Embryonic and tumorigenic pathways converge via Nodal signaling: role in melanoma aggressiveness," Nature Medicine, vol. 12, No. 8, Aug. 2006, pp. 925-932.

Hendrix Mary J. C. et al.: "Reprogramming metastatic tumor cells with embryonic microenvironments," Nature Reviews Cancer, vol. 7, No. 4, Apr. 2007, pp. 246-255.

Cochlovius, et al., Therapeutic Antibodies: After Years of Promise, Magic Bullets Appear to be on the Upswing, *Modern Drug Delivery*, 6(10):34-34 & 37-38, 2003.

Glennie, et al., Clinical Trials of Antibody Therapy, *Immunology Today*, 21(8):403-410, 2000.

Kosaki, et al., Characterization and Mutation of Analysis of Human LEFTY A and LEFTY B, Homologues of Murine Genes Implicated in Left-Right Axis Development, *Am. J. Hum. Genet.*, 64:712-721, 1999.

Strizzi, et al., Nodal as a Biomarker for Melanoma Progression and a New Therapeutic Target for Clinical Intervention, *Expert Rev. Dermatol.*, 4(1):67-78, 2009.

Weiner, et al., New Approaches to Antibody Therapy, *Oncogene*, 19:6144-6151, 2000.

International Search Report from PCT/US2007/074529 dated Jan. 14, 2008, 3 pages.

* cited by examiner

A

B

C
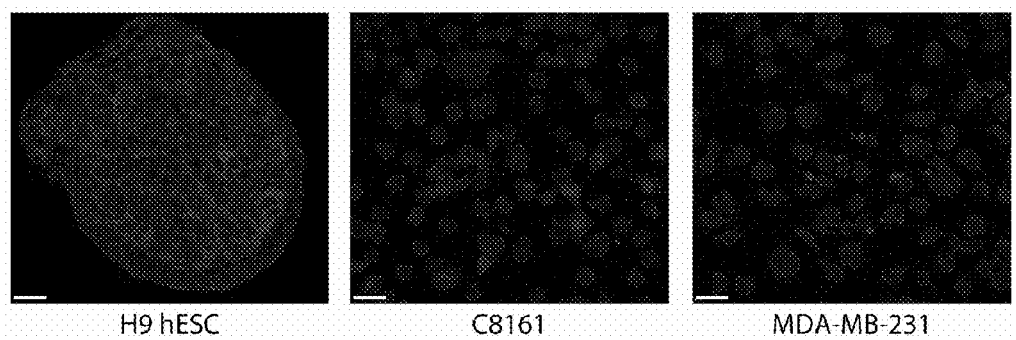
D
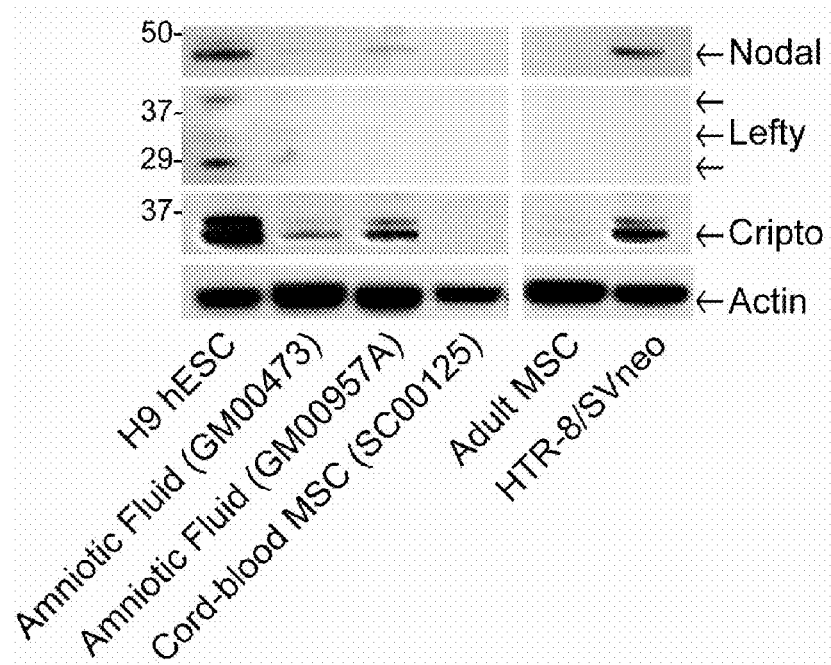
Figure 5 (con't.)

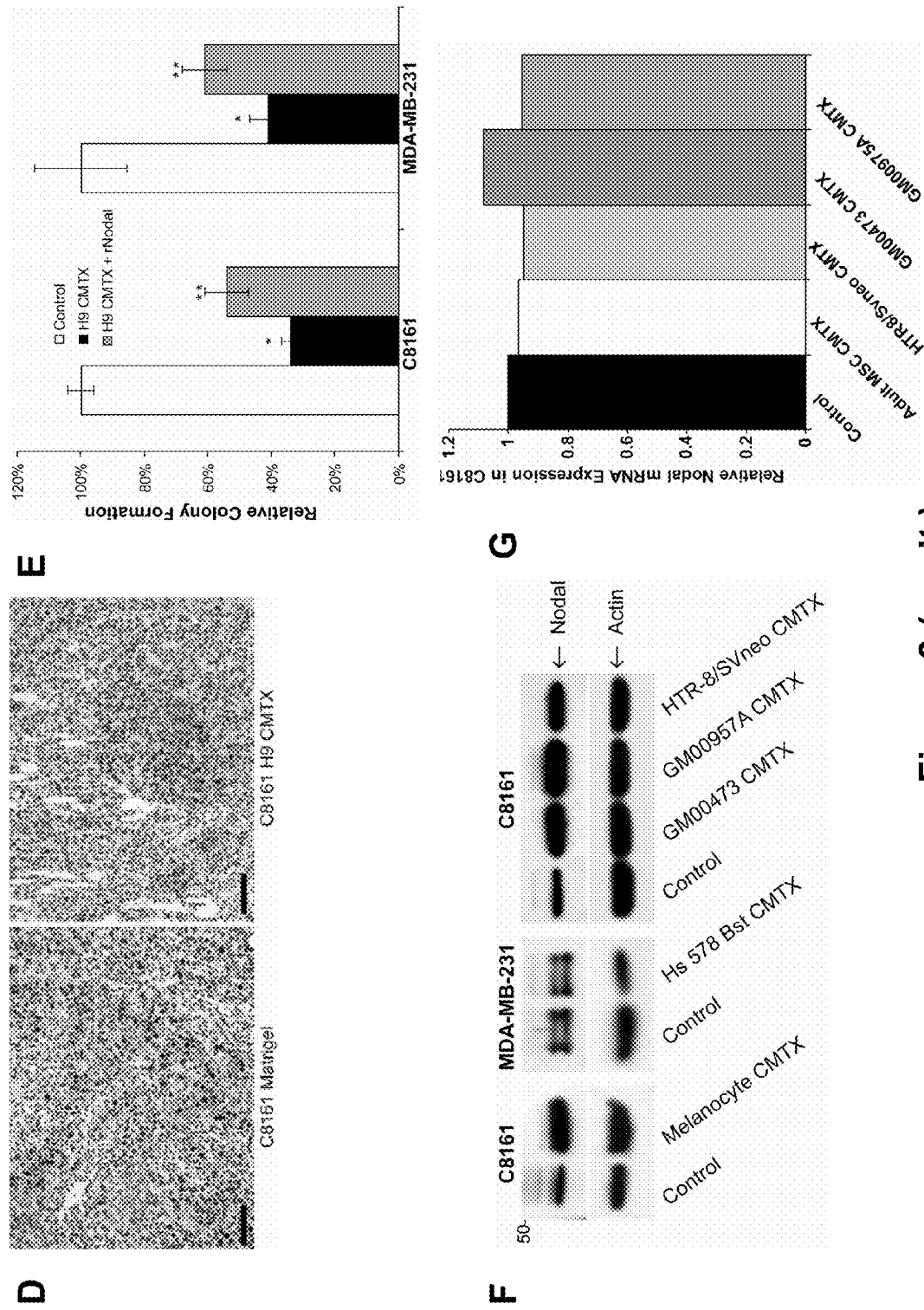
Figure 9 (con't.)

E
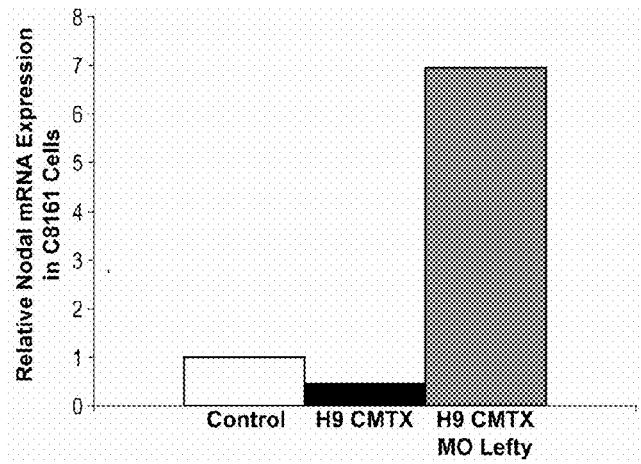
F
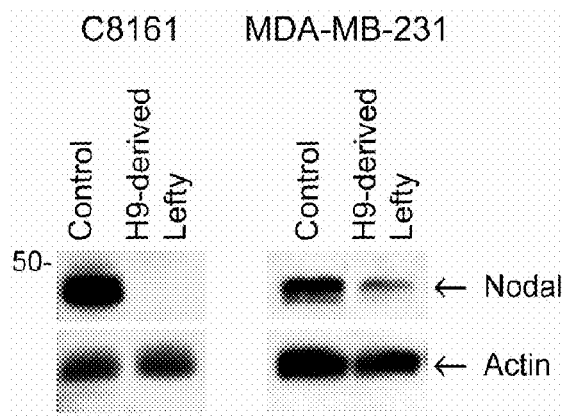
G
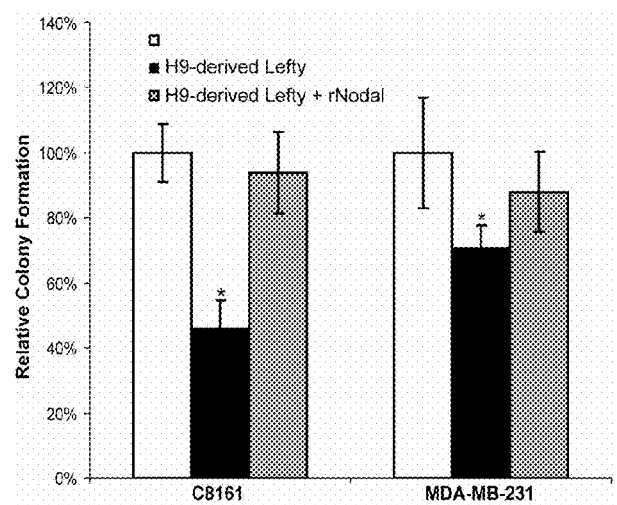
Figure 10 (con't.)

A

B

METHODS OF INHIBITING TUMOR CELL AGGRESSIVENESS USING THE MICROENVIRONMENT OF HUMAN EMBRYONIC STEM CELLS

CROSS REFERENCE TO RELATED APPLICATIONS

This application is a continuation-in-part of U.S. patent application Ser. No. 11/829,070, filed Jul. 26, 2007, which claims the benefit of U.S. Provisional Patent Application Nos. 60/820,740, filed on Jul. 28, 2006, and 60/941,343, filed on Jun. 1, 2007, the disclosures of which are incorporated by reference herein.

FIELD OF THE INVENTION

The invention relates to methods of using compounds produced by embryonic stem cells to treat and/or prevent the growth and/or dissemination of aggressive tumor cells in a patient. More specifically, the invention relates to the administration to the patient of inhibitors of Nodal activity, including, but not limited to, those that are exclusively produced by human embryonic stem cells. The invention also relates to methods for detecting aggressive tumors in a patient comprising detecting the presence of Nodal in the patient's cells.

BACKGROUND

Aggressive tumor cells share a number of characteristics with embryonic progenitors. During vertebrate development, multipotent precursor cells are gradually specified to particular fates through the autocrine or paracrine delivery of signaling molecules, and during cancer progression, malignant cells similarly release and receive cues that promote tumor growth and metastasis. Aggressive tumor cells, particularly melanoma cells, display stem cell-like plasticity as demonstrated by their molecular signature that signifies a dedifferentiated, multipotent plastic phenotype (i.e. one that is capable of responding to microenvironmental factors as well as influencing other cells via epigenetic mechanisms) (Bittner et al., 2000, *Nature* 406:536-540; Hendrix et al., 2003, *Nat. Rev. Cancer* 3:411-421). Furthermore, aggressive melanoma cells are capable of vasculogenic mimicry, i.e. they are able to form vasculogenic-like networks while simultaneously expressing genes associated with an endotheilial cell type. (Seftor et. al., 2002, Crit. Rev. Oncology Hematol. 44:17-27; Maniotis et. al., Am. J. Pathol. 155:739-752).

Previous studies capitalized on the similarities between cancer and stem cells by examining the ability of embryonic microenvironments to modulate tumor cell behavior (Pierce et al., 1982, *Cancer Res.* 42:1082-1087; Gerschenson et al., 1986, *Proc. Natl. Acad. Sci. U.S. A* 83:7307-7310; Lee et al., 2005, *Dev. Dyn.* 233:1560-1570; Mintz et al., 1975, *Proc. Natl. Acad. Sci. U.S. A* 72:3585-3589). For example, Pierce and colleagues reported that neural stage mouse embryos regulate neuroblastoma cells, and that embryonic skin inhibits melanoma growth ((Pierce et al., 1982, *Cancer Res.* 42:1082-1087; Gerschenson et al., 1986, *Proc. Natl. Acad. Sci. U.S. A* 83:7307-7310). Although studies have focused on the role of embryonic signals in the regulation of tumor cells, few have utilized embryonic models as a tool to discover molecular mechanisms by which cancer cells modulate their microenvironment and the resulting reciprocal interactions.

One of the major factors contributing to the plasticity of stem cells is Nodal. Nodal is a highly conserved morphogen belonging to the transforming growth factor beta (TGFβ) super family (Schier et al., 2003, *Annu. Rev. Cell Dev. Biol.* 19:589-621). By acting as an organizing signal before gastrulation, Nodal initiates embryonic axis formation, and previous studies demonstrated that the ectopic expression of Nodal induces mesendodermal fates in ectopic positions (Whitman, 2001, *Dev. Cell* 1:605-617; Schier, 2003, *Annu. Rev. Cell Dev. Biol.* 19:589-621; Iannaccone et al., 1992, *Dev. Dyn.* 194:198-208; Smith, 1995, *Curr. Opin. Cell Biol.* 7:856-861; Zhou et al., 1993, *Nature* 361:543-547; Rebagliati et al., 1998, *Proc. Natl. Acad. Sci. U.S.A* 95:9932-9937; Toyama et al., 1995, *Development* 121:383-391).

Activation of Nodal includes binding to the co-receptor Cripto and subsequent phosphorylation of the type I and type II activin-like kinase receptors (ALK). In turn, SMAD2 and SMAD3 are activated (Lee et. al., 2006, Nature Medicine 12:882-884). Furthermore, human embryonic stem cells express Nodal and secrete endogenous inhibitors of Nodal such as Lefty A/B (Besser, D., 2004, *J. Biol. Chem.* 279: 45076-45084). Lefty A and Lefty B, human homologs to murine Lefty 2 and Lefty 1, respectively, are separated by approximately 50 kb on chromosome q42 and are 96% identical to each other (Kosaki et. al., 1999, Am. J. Hum. Genet. 64:712-21). Lefty A and Lefty B are members of the TGFβ superfamily, and are considered one of the powerful inhibitors of Nodal.

SUMMARY OF THE INVENTION

The invention provides compositions comprising one or more isolated factors from a microenvironment of human embryonic stem cells (hESCs), including, but not limited to, Lefty and inhibitors of Nodal. The invention further provides an isolated Lefty protein produced by conditioning a matrix with human embryonic stem cells. The invention further provides a protein comprising glycosylated Lefty, including glycosylated Lefty isolated from the microenvironment of human embryonic stem cells, compositions thereof, and methods of inhibiting tumor cell growth in a mammal comprising administering to the mammal such compositions.

The invention also provides methods of utilizing factors derived from human embryonic stem cells (hESC) and their microenvironment to treat and prevent tumor formation and progression and to inhibit tumor cell aggressiveness. The invention further provides methods of inhibiting tumor cell growth and/or treating aggressive tumors in a mammal comprising administering to the mammal, having at least one tumor cell present in its body, an effective amount of an inhibitor of Nodal activity, including, but not limited to, hESC-derived Lefty and synthetic derivatives as discussed herein, glycosylated Lefty, recombinant Lefty, anti-Nodal antibodies, inhibitors of one or more of activin receptor-like proteins ALK 4, ALK 5, and/or ALK7, inhibitors of Cripto, anti-Nodal antisense moieties such as anti-Nodal Morpholinos, and Notch inhibitors including, but not limited to, Notch 4 inhibitors such as Notch 4 siRNA.

The invention also provides a method of inhibiting tumor cell growth in a mammal comprising administering to the mammal, having at least one tumor cell present in its body, an effective amount of a preconditioned microenvironment, which has been in contact with human embryonic stem cells.

The invention further provides methods for detecting aggressive tumors (including but not restricted to melanoma and breast carcinoma) in a patient comprising the steps of: obtaining a sample from a patient; assaying the sample for the presence of Nodal and the absence of a Nodal inhibitor (such as Lefty or modified Lefty or Lefty derivatives); and detecting aggressive tumor cells if Nodal is present and Lefty is absent in the sample. The invention also provides methods of identifying compounds for treating aggressive tumors comprising providing a plurality of cells that express Nodal; assaying the cells in the presence and absence of a candidate compound for activity of Nodal; and identifying the compound as a compound for treating aggressive tumors if the Nodal activity is less in the presence of the candidate compound than in the absence of the candidate compound.

In addition, the invention provides methods for monitoring the effectiveness of a pharmaceutical composition as an agent for treating aggressive tumors in a patient, for detecting the presence of aggressive tumor cells, and for methods for detecting the presence of cells having a dedifferentiated, multipotent plastic phenotype in a mammal Specific embodiments of the invention will become evident from the following more detailed description of certain preferred embodiments and the claims.

BRIEF DESCRIPTION OF THE DRAWINGS

FIGS. 6 (A-F) show immunohistochemical analysis of Nodal staining in (A) normal skin, (B-D) a primary cutaneous melanoma and (E and F) cutaneous melanoma metastases. Arrows delineate (A) normal melanocytes and (F) Nodal protein localized to melanoma cell membranes. (C) and (D) represent radial and vertical growth phases respectively. FIG. 6(A-D) are representative of 5 patient samples and FIG. 6(E-F) are representative of 10 patient samples. Isotype controls are pictured in the insets, and bars equal 50 µm.

DETAILED DESCRIPTION

Figure 1:
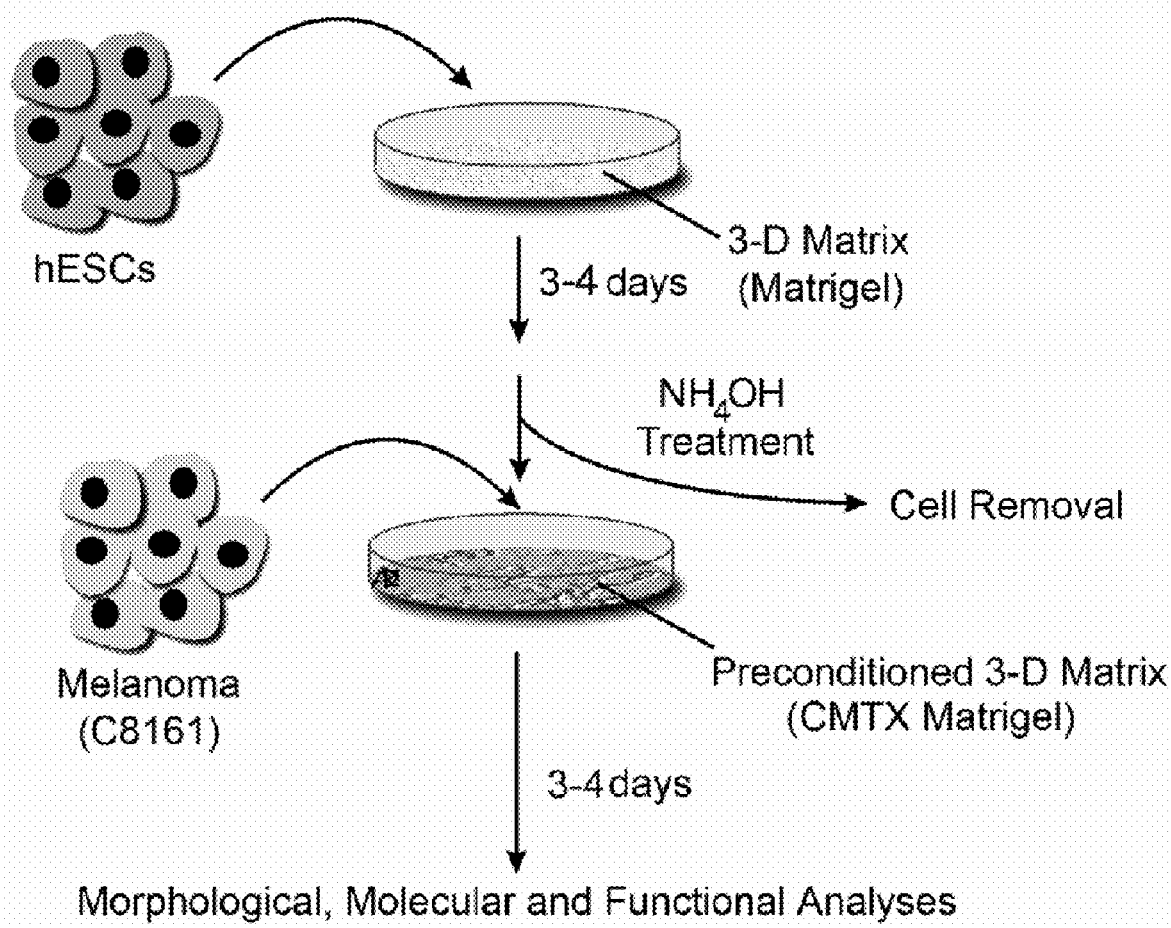
FIG. 1 shows an experimental methodology flow chart demonstrating the utilization of human embryonic stem cell microenvironments to inhibit tumor cell aggressiveness.

In certain embodiments, the invention provides a composition comprising one or more isolated factors from a microenvironment of human embryonic stem cells (hESCs). As used herein, "one or more isolated factors" refers to any one or any group of factors present in a microenvironment of hESCs. The factors may be individually isolated, or isolated in a manner that provides a group of factors in combination. Alternatively, "one or more isolated factors" may refer to any one or a group of factors present on a defined matrix. As used herein, a "microenvironment" is an environment that comprises a basement membrane or other defined matrix that is in contact with embryonic stem cells, preferably human embryonic stem cells, and that is influenced by the embryonic stem cells. A "preconditioned" microenvironment is a microenvironment that has been in contact with human embryonic stem cells under appropriate conditions as described herein, and described for example, in Postovit et al., 2006, Stem Cells 24:501-505 and illustrated in FIG. 1 herein. FIG. 1 herein illustrates utilization of human embryonic stem cell microenvironments to inhibit tumor cell aggressiveness.

In one embodiment, the isolated factor(s) from a microenvironment of hESCs inhibit Nodal. As described herein, aggressive tumor cells express Nodal, and Nodal is essential for plasticity, tumorgenicity and aggressiveness. Therefore, inhibiting Nodal provides an excellent approach for treating and preventing aggressive tumors. As used herein, the terms "aggressive tumor" and "aggressive cancer," which include "aggressive melanoma" and "aggressive breast carcinoma" refer to a malignant cell that has neoplastic growth with or without metastatic involvement. In a non-limiting example, an aggressive tumor may refer to a malignant cell that has a transdifferentiated phenotype characterized by the aberrant expression of genes normally restricted to other cell lineages, concomitant with the loss of lineage-specific factors. For example, aggressive melanoma cells possess keratin-positive, intermediate filaments indicative of epithelial cells, and they aberrantly express genes, including VE-Cadherin, normally associated with endothelial cells. Furthermore, the expression of melanocyte specific markers, such as Tyrosinase, is dramatically reduced, and sometimes absent, in aggressive melanoma cells. Tyrosinase catalyses the conversion of tyrosine to the pigment melanin, and is reduced by more than 35-fold in aggressive melanomas as compared to their poorly aggressive counterparts. Aggressive tumor cells also have the ability to express multiple stem cell markers, suggestive of a multipotent, dedifferentiated phenotype. These aggressive tumor cells are also highly metastatic.

In one embodiment of the invention, the factor from a microenvironment of hESCs is Lefty. As noted herein, Lefty, including hESC-derived Lefty, is an inhibitor of Nodal. As used herein, the terms "Lefty A/B" and "Lefty" are interchangeable and refer to either Lefty A or Lefty B, or both Lefty A and Lefty B in combination. In one embodiment, Lefty, isolated from a microenvironment, may be substantially pure. In another embodiment, Lefty may be present in combination with other hESC factors. As used herein, by "substantially pure" it is meant a preparation which is at least 70% by weight (dry weight) the compound of interest, i.e., hESC-derived Lefty. Preferably the preparation is at least 75%, more preferably at least 90%, and most preferably at least 99%, by weight the compound of interest. Purity can be measured by any appropriate method, e.g., column chromatography, polyacrylamide gel electrophoresis, or HPLC analysis.

In another embodiment, the invention provides an isolated Lefty protein produced by conditioning a matrix with human embryonic stem cells. As used herein, "conditioning a matrix" refers to preparing a preconditioned microenvironment as defined herein. In certain embodiments, the matrix is conditioned with hESCs from 0 to 10 days or any range in between, including, but not limited to, from 0.5 to 10 days, from 2 to 8 days, from 3 to 6 days, from 3 to 5 days, from 3 to 4 days, or for 1, 2, 3, 4, or 5 days. Lefty may be isolated from the matrix by any method known to one of skill in the art, including through use of anti-Lefty antibodies.

In one embodiment, the invention provides a protein comprising glycosylated Lefty. In this embodiment, Lefty may be glycosylated to varying degrees, and may comprise one or more N- and/or O-linked glycosylation sites, or a combination thereof. In one embodiment, the glycosylated Lefty is characterized in that more than 0%, 5%, 10%, 15%, 20%, 25%, 30%, 35%, 40%, 45%, 50%, 55%, 60%, 65%, 70%, 75%, 80%, 85%, 90%, or 95% of the possible N- and/or O-glycosylation sites are glycosylated. In another embodiment, the glycosylated Lefty is characterized in that less than 100%, 95%, 90%, 85%, 80%, 75%, 70%, 65%, 60%, 55%, 50%, 45%, 40%, 35%, 30%, 25%, 20%, 15%, 10%, or 5% of the possible N- and/or O-glycosylation sites are glycosylated. In another embodiment, the glycosylated Lefty is characterized in that the percentage of possible N- and/or O-glycosylation sites that are glycosylated is based on a combination of the "more than" and "less than" percentages recited above. Thus, in one non-limiting example, the glycosylated Lefty is characterized in that more than 30% and less than 70% of the possible N- and/or O-glycosylation sites are glycosylated. In another embodiment, 100% of the possible N- and/or O-glycosylation sites are glycosylated.

In one embodiment, the glycosylated Lefty is glycosylated to substantially the same extent as Lefty derived from hESCs.

Glycosylated Lefty may be prepared by any method, including by recombinant methods (see, e.g. Sambrook et al., 2001, *Molecular Cloning: A Laboratory Manual*, 3rd ed., Cold Spring Harbor Laboratory Press, Cold Spring Harbor, N.Y.). In one embodiment, glycosylated Lefty is prepared recombinantly in Chinese Hamster Ovary (CHO) cells. Alternatively, glycosylated Lefty may be prepared by chemical synthesis methods (such as solid phase peptide synthesis) using techniques known in the art such as those set forth by Merrifield et al., 1963, J. Am. Chem. Soc. 85:2149; Houghten et al., 1985, Proc Natl Acad. Sci. USA 82:5132; and Stewart and Young, Solid Phase Peptide Synthesis (Pierce Chemical Co. 1984), or by a combination of synthetic and recombinant techniques. Glycosylated Lefty may also be prepared by isolation from hESCs, including by isolation from the microenvironment of hESCs.

Included within the scope of the invention are fragments or derivatives of Lefty or glycosylated Lefty. As used herein, "fragment" means any portion of the full length Lefty sequence having an activity of the full length protein, including, but not limited to, the ability to inhibit Nodal. Included in the scope of "fragments" are naturally occurring enzymatic cleavage products. Included in the scope of the term "derivatives" are derivatives of full length Lefty as well as fragments thereof. As used herein, "derivative" or "derivatives" includes variations of Lefty having one or more amino acid residues which have been added, deleted, inserted or substituted, where the resulting polypeptide has an activity of Lefty, including, but not limited to, the ability to inhibit Nodal. As used herein, "derivatives" also includes chemical derivatives of Lefty and variations thereof. It will be understood to one of skill in the art that these variations may occur in any combination.

Chemically modified derivatives of glycosylated Lefty may be prepared by one skilled in the art, in view of the disclosures described herein. Glycosylated Lefty derivatives are modified in a manner that is different—either in the type or location of the molecules naturally attached to the polypeptide. Derivatives may include molecules formed by the deletion of one or more naturally-attached chemical group, or they may be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water-soluble polymer, some molecules will weigh more, some less, than the stated molecular weight). The average molecular weight of each polymer is preferably between about 5 kDa and about 50 kDa, more preferably between about 12 kDa and about 40 kDa and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-($C_1$-$C_{10}$), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules which may be used to prepare covalently attached glycosylated Lefty polypeptide multimers.

In general, chemical derivatization may be performed under any suitable condition used to react a protein with an activated polymer molecule. The optimal reaction conditions will be determined based on known parameters and the desired result. For example, the larger the ratio of polymer molecules to protein, the greater the percentage of attached polymer molecule. In one embodiment, the glycosylated Lefty derivative may have a single polymer molecule moiety at the amino-terminus. See, e.g., U.S. Pat. No. 5,234,784.

The pegylation of a polypeptide may be specifically carried out using any of the pegylation reactions known in the art. Such reactions are described, for example, in the following references: Francis et al., 1992, Focus on Growth Factors 3:4-10; European Patent Nos. 0154316 and 0401384; and U.S. Pat. No. 4,179,337.

In another embodiment, glycosylated Lefty polypeptides may be chemically coupled to biotin. The biotin/glycosylated Lefty polypeptide molecules are then allowed to bind to avidin, resulting in tetravalent avidin/biotin/glycosylated Lefty polypeptide molecules. Glycosylated Lefty polypeptides may also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions that may be alleviated or modulated by the administration of the present glycosylated Lefty derivatives include those described herein for glycosylated Lefty. However, the glycosylated Lefty derivatives disclosed herein may have additional activities, enhanced or reduced biological activity, or other characteristics, such as increased or decreased half-life, as compared to the non-derivatized molecules.

In a further embodiment, the present invention provides a composition comprising a glycosylated Lefty. Compositions may be formulated as known to one of skill in the art or as described herein. In another embodiment, the present invention provides methods of inhibiting tumor cell growth in a mammal comprising administering to the mammal a composition comprising a glycosylated Lefty at a physiologically acceptable dosage. Such a composition may be administered in an effective or therapeutically effective amount. As used herein, "effective amount" and "therapeutically effective amount" are used interchangeably.

By mammal it is meant humans, companion animals such as cats and dogs, primates such as monkeys and chimpanzees, and livestock animals such as horses, cows, pigs, and sheep, or any patient in need of, or that will benefit from, administration of any of the methods or compounds or compositions of the invention. The term "patient" as used herein includes human and animal subjects.

In one embodiment, the invention comprises methods of inhibiting tumor cell growth in a mammal comprising administering to the mammal a composition comprising a glycosylated Lefty at a dosage between 0.01 and 500 ng/mL, between 0.01 and 200 ng/mL, between 0.1 and 200 ng/mL, between 0.1 and 100 ng/mL, between 1 and 100 ng/mL, between 10 and 100 ng/mL, between 10 and 75 ng/mL, between 20 and 75 ng/mL, between 20 and 50 ng/mL, between 25 and 50 ng/mL, or between 30 and 40 ng/mL. In another embodiment, the invention comprises methods of inhibiting tumor cell growth in a mammal comprising administering to the mammal a composition comprising a glycosylated Lefty at a dosage of about 1, 5, 10, 20, 25, 30, 35, 40, 45, 50, 75, 100, 200, or 500 ng/mL. As used in this context, "about" means within 0, 1, 2, or 3 ng/mL of the recited concentration.

In certain embodiments, the invention provides methods of using one or more factors from a microenvironment of human embryonic stem cells to inhibit tumor cell aggressiveness. In one embodiment, the factor(s) is an inhibitor of Nodal, including, but not limited to Lefty and glycosylated Lefty.

In one embodiment of these methods, the factor(s) inhibiting tumor cell aggressiveness do so by increasing apoptosis.

As used herein, "apoptosis" refers to the physiologic process of programmed cell death which normally occurs during embryonic development and during maintenance of tissue homeostasis. In a further embodiment, the factor(s) inhibiting tumor cell aggressiveness do so by decreasing cell proliferation. Cell proliferation is defined as the increase in number of cells resulting from completion of the cell cycle, as contrast to growth, which is the increase in the individual cell mass. In a further embodiment, the factor(s) inhibiting tumor cell aggressiveness do so by both increasing apoptosis and by decreasing cell proliferation and/or by decreasing the tumor cell proliferation-to-apoptosis ratio.

In another embodiment, the invention provides a method of inhibiting tumor cell growth in a mammal comprising administering to the mammal, having at least one tumor cell present in its body, an effective amount of a preconditioned microenvironment, which has been in contact with human embryonic stem cells.

In further embodiments of the invention, Nodal and/or Lefty are used as biomarkers for aggressive tumor cell aggressiveness and for prognostic, diagnostic and clinical diagnoses for aggressive carcinoma including, but not limited to, melanoma and breast cancer. In certain embodiments, the invention provides methods for detecting aggressive tumors (including but not restricted to melanoma or breast cancer) in a patient comprising the steps of: obtaining a sample from a patient; assaying the sample for the presence of Nodal and Lefty; and detecting aggressive tumors if Nodal is present and Lefty is absent in the sample. As used in this context, "a sample" includes, but is not limited to, tumor cells, tissue samples, and bodily fluids as defined herein. In a non-limiting example, the sample can be serum.

In certain embodiments, the presence of Nodal can be detected by assaying for the Nodal gene or gene product. For example, a nucleic acid based assay or a protein based assay can be used to detect the presence of Nodal in a tumor sample. Exemplary assays that can be used to detect Nodal include those described herein. The presence of Lefty can be similarly detected. Those of skill in the art readily recognize that other assays can be designed following conventional methods as described, for example, in Sambrook et al., 2001, *Molecular Cloning: A Laboratory Manual*, 3rd ed., Cold Spring Harbor Laboratory Press, Cold Spring Harbor, N.Y.

In another embodiment, compounds for treating aggressive tumors may be identified by providing a plurality of cells that express Nodal, assaying the cells for Nodal activity in the presence and absence of a candidate compound, and identifying the compound as a compound suitable for treating aggressive tumors if the Nodal activity is less in the presence of the compound than in the absence of the candidate compound. As used in this context, "Nodal activity" refers Nodal expression and/or to any of the activities recited herein, including maintaining tumor cell plasticity, tumorgenicity and aggressiveness.

In another method of the invention, the effectiveness of a pharmaceutical composition as an agent for treating aggressive tumors in a patient may be monitored. The method comprises obtaining a first sample from a patient; assaying the first sample for the presence of Nodal; administering an amount a pharmaceutical composition to the patient; assaying subsequently-collected biological samples from the patient for the presence of Nodal; and comparing the amount of Nodal detected in the first sample with the amount of Nodal detected in the subsequent samples, wherein the effectiveness of the pharmaceutical composition is monitored by detecting changes in the amount of Nodal in the subsequently-collected samples compared with the first sample. As used in this context, "a sample" or "biological sample" includes, but is not limited to, tumor cells, tissue samples, and bodily fluids as defined herein. In a non-limiting example, the sample can be serum.

In another method of the invention, the presence of aggressive tumor cells in a mammal may be detected by obtaining a sample of tumor cells from a patient; conducting a sequence based methylation analysis of the Nodal CpG island in the tumor cells; comparing the degree of methylation in the CpG island of Nodal in the tumor cells to that of non-aggressive or non-tumor cells; and correlating hypermethylation of Nodal with the presence of aggressive tumor cells. The sequence based methylation analysis may be based on the entirety of the CpG island or on a subsection thereof. In a further method of the invention the presence of cells having a dedifferentiated, multipotent plastic phenotype in a mammal may be detected by obtaining a sample from a mammal; assaying the sample for the presence of Nodal; and correlating the presence of Nodal with the presence cells having a dedifferentiated, multipotent plastic phenotype. The sample may be a bodily fluid. Bodily fluids include, but are not limited to, whole blood, blood plasma, blood serum, urine, semen, saliva, lymph fluid, meningal fluid, amniotic fluid, glandular fluid, sputum and cerebrospinal fluid. Bodily fluid also includes experimentally separated fractions of all of the preceding and solutions or mixtures containing homogenized solid material, such tissues and biopsy samples. These methods may be used as a prognostic or diagnostic assay for aggressive cancer or susceptibility to aggressive cancer, including, but not limited to, melanoma and breast cancer.

In other embodiments, the invention provides methods of inhibiting tumor cell growth in a mammal comprising administering to the mammal, having at least one tumor cell present in its body, an effective amount of an inhibitor of Nodal activity.

The invention also provides methods of treating aggressive tumors in a mammal comprising administering to the mammal, having at least one tumor cell present in its body, an effective amount of an inhibitor of Nodal activity. As used herein, the phrase "treating aggressive tumors" refers to a method comprising administering a Nodal inhibitor to a mammal in need thereof, wherein the Nodal inhibitor prevents aggressive tumor cell growth, and/or prevents aggressive tumor cell metastasis in the mammal.

In another embodiment, the invention also provides methods of treating tumors in a mammal comprising administering to the mammal, having at least one tumor cell present in its body, an effective amount of Lefty derived from human embryonic stem cells. In a further embodiment, the hESC-derived Lefty is substantially free of other factors in the hESC microenvironment. In another embodiment, the tumor is melanoma or breast cancer.

In one embodiment, the invention provides methods of inhibiting tumor cell growth and/or treating aggressive tumors comprising contacting the tumor cell with a microenvironment that comprises human embryonic stem cells or a microenvironment that has been preconditioned by human embryonic stem cells ("CMTX"). In certain embodiments, the basement membrane matrix can be Matrigel™. There is variability between lots of Matrigel basement membrane matrix, which can impact the preparation of the preconditioned media. More specifically, occasional lots of Matrigel will not produce a preconditioned microenvironment that has the tumor inhibiting properties of the invention. In such situations, an alternate lot can be used. One of skill in the art will understand that other matrices may be used.

As used herein, an "inhibitor" can be any chemical compound, nucleic acid molecule, endogenous protein such as Lefty A/B, peptide or polypeptide such as an antibody against Nodal that can reduce Nodal activity or interfere with expression of a Nodal gene. Included within the scope of the term "inhibitor" is any combination of two or more such inhibitors administered concurrently or separately and in any order. A Nodal inhibitor can inhibit the activity of a Nodal protein either directly or indirectly. Direct inhibition can be accomplished, for example, by binding to a Nodal protein and thereby preventing the Nodal protein from binding an intended target, such as a receptor. Indirect inhibition can be accomplished, for example, by binding to a Nodal protein's intended target, such as a receptor or binding partner, thereby blocking or reducing activity of the Nodal protein. Furthermore, a Nodal inhibitor can inhibit a Nodal gene by reducing or inhibiting expression of the gene, inter alia by interfering with gene expression (transcription, processing, translation, post-translational modification), for example, by interfering with the Nodal mRNA and blocking translation of the Nodal gene product or by post-translational modification of the Nodal gene product, or by causing changes in intracellular localization.

A Nodal inhibitor can also be an endogenously produced protein, including but not restricted to, Lefty A/B derived from the microenvironment of human embryonic stem cells. For example, Lefty A/B is produced in human embryonic stem cells and is secreted into the microenvironment surrounding the cells. Lefty A/B can be isolated from the microenvironment. Alternatively, Lefty A/B can be isolated from the human embryonic stem cells directly (i.e. before it is secreted into the microenvironment). In a further embodiment, a synthetic Lefty may be prepared by any technique known in the art such that it is identical to hESC-derived Lefty. In another embodiment, a Nodal inhibitor within the scope of the invention is recombinant Lefty A/B (rLefty) that may be prepared by any conventional methods known in the art. Lefty A/B may be glycosylated or non-glycosylated. In certain embodiments, Nodal inhibitors in accordance with the invention are glycosylated Lefty A/B produced by hESCs. In other embodiments, glycosylated Lefty A/B may be prepared by using CHO (Chinese Hamster Ovary) cells. In some instances, glycosylated Lefty A/B may be a more potent inhibitor of Nodal than its non-glycosylated or recombinant counterpart, and may therefore be administered in therapeutic applications at a lower dose.

In other embodiments, Nodal inhibitors are molecules which interfere with Nodal signaling, such as activin-like kinase (ALK) inhibitors. For example, Nodal propagates its signal by binding to heterodimeric complexes between type I (ALK 4/5/7) and type II (ActRIIB) activin-like kinase receptors. Assembly of the complex causes phosphorylation and activation of ALK 4/5/7 by ActRIIB, which is followed by ALK 4/5/7 mediated phosphyorylation of Smad-2/3. Inhibitors of ALK 4, ALK 5, and/or ALK7 are included within the scope of the invention; as described herein, ALK 4/5/7 inhibitors can abrogate Nodal expression. In one embodiment, the ALK inhibitor is SB431542 (Sigma, St. Louis, Mo.).

In one embodiment, an inhibitor can be, for example, a small molecule inhibitor, an antibody, a nucleic acid such as an antisense oligonucleotide, a short interfering RNA (siRNA) molecule, or a short hairpin RNA (shRNA) molecule. In addition, such inhibitors can be specifically designed using the methods described herein or using methods known in the art.

In certain embodiments, an antisense oligonucleotide is complementary to at least a portion of a Nodal gene, so long as hybridization of the antisense oligonucleotide inhibits Nodal activity. The term "oligonucleotide" as used herein includes naturally occurring, and modified nucleotides linked together by naturally occurring, and/or non-naturally occurring oligonucleotide linkages. Oligonucleotides are a polynucleotide subset generally comprising no more than 200 nucleotides. In certain embodiments, oligonucleotides are 10 to 60 nucleotides in length. In certain embodiments, oligonucleotides are 12, 13, 14, 15, 16, 17, 18, 19, 20, 21, 22, 23, 24, 25, or 30 to 40 bases in length. Oligonucleotides are single stranded, e.g. for use in the construction of a gene mutant using site directed mutagenesis techniques.

The oligonucleotides of the invention may also comprise nucleotide analogs that may be better suited as therapeutic or experimental reagents. An example of an oligonucleotide analogue is a peptide nucleic acid (PNA) wherein the deoxyribose (or ribose) phosphate backbone in the DNA (or RNA), is replaced with a polyamide backbone which is similar to that found in peptides (P. E. Nielsen, et al Science, 1991, 254, 1497). PNA analogues have been shown to be resistant to degradation by enzymes and to have extended lives in vivo and in vitro. PNAs also bind stronger to a complimentary DNA sequence due to the lack of charge repulsion between the PNA strand and the DNA strand. Other oligonucleotides may contain nucleotides containing polymer backbones, cyclic backbones, or acyclic backbones. For example, the nucleotides may have morpholino backbone structures (U.S. Pat. No. 5,034,506). Oligonucleotides may also contain groups such as reporter groups, a group for improving the pharmacokinetic properties of an oligonucleotide, or a group for improving the pharmacodynamic properties of an oligonucleotide. Oligonucleotides may also have sugar mimetics.

The antisense nucleic acid molecules may be constructed using chemical synthesis and enzymatic ligation reactions using procedures known in the art. The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

In one embodiment, the Nodal inhibitors of the invention are anti-Nodal Morpholinos.

In one embodiment, certain inhibitors provided by the invention are species of short interfering RNA (siRNA). The term "short interfering RNA" or "siRNA" as used herein refers to a double stranded nucleic acid molecule capable of RNA interference or "RNAi", as disclosed, for example, in Bass, 2001, Nature 411: 428-429; Elbashir et al., 2001, Nature 411: 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914. As used herein, siRNA molecules need not be limited to those molecules containing only RNA, but further encompasses chemically modified nucleotides and non-nucleotides having RNAi capacity or activity. Specific siRNA molecules that inhibit Nodal activity can be designed using methods known to those of skill in the art or commercially available technology (such as technology provided by Dharmacon Research, Lafayette, Colo.).

In another embodiment, the Nodal inhibitors of the invention include any chemical compounds, nucleic acids, proteins, peptides, polypeptides, antibodies, or other molecules that inhibit Notch. In certain embodiments, the Nodal inhibitors are Notch4 inhibitors. In certain embodiments the Nodal inhibitors are Notch siRNAs. In certain embodiments, the Nodal inhibitors are Notch4 siRNAs.

In certain embodiments, the invention provides antibodies or immunologically functional fragments thereof that selectively bind to Nodal and methods for selectively inhibiting or interfering with the activity of Nodal proteins. Standard methods for preparation of monoclonal and polyclonal antibodies and immunologically active fragments thereof are well known in the art, for example as described in Harlow and Lane (1988, ANTIBODIES: A LABORATORY MANUAL, Cold Spring Harbor Laboratory Press: New York). Methods for generating antibody fragments, particularly Fab fragments and other fragments that retain epitope-binding ability and specificity are also well known, as are fully human antibodies and chimeric antibodies, including "humanized" antibodies. "Humanized" antibodies include, for example, antibodies generated in mice that are "humanized" to reduce negative immune effects that can occur during administration to human subjects by replacing certain portions of the mouse antibody with portions of human antibodies. Thus, the invention encompasses use of antibody inhibitors of Nodal that include, but are not limited to, single chain antibodies, single chain Fv antibodies, F(ab) antibodies, F(ab)' antibodies and (Fab')$_2$ antibodies, chimeric antibodies in which one or more regions have been replaced by homologous human or non-human portions, and fully human antibodies. Single chain antibodies are discussed in detail in International Patent Application Publication No. WO 88/01649 and U.S. Pat. Nos. 4,946,778 and 5,260,203. Such inhibitors can be delivered, for example, via a penetratin tag (HIV or antennaepedia) or by recombinant means (e.g. encoded by a polynucleotide introduced into a cell in a viral vector).

In preferred embodiments, methods of the invention comprise the step of administering a pharmaceutical composition comprising an effective amount of one or a plurality of Nodal inhibitors together with a pharmaceutically acceptable diluent, carrier, solubilizer, emulsifier, preservative and/or adjuvant, wherein the pharmaceutical composition is capable of inducing a desired therapeutic effect when properly administered to a patient. Preferably, acceptable formulation materials are nontoxic to recipients at the dosages and concentrations employed.

The expression "effective amount" in reference to a pharmaceutical composition comprising one or a plurality of Nodal inhibitors is understood to mean, according to the invention, an amount of the said pharmaceutical composition that is capable of preventing or reducing growth of aggressive melanoma cells. For example, a pharmaceutical composition is therapeutically effective where a patient who has aggressive melanoma has a reduced number of melanoma cells and/or reduced metastases of melanoma cells after treatment with the pharmaceutical composition compared with prior to said treatment. A pharmaceutical composition administered to a patient is also therapeutically effective where metastases of melanoma cells are prevented from occurring in a patient who has melanoma, has a history of melanoma (e.g. patient is in remission), or who is considered likely to present with melanoma (e.g. has a genetic disposition favoring onset of melanoma).

In certain embodiments, a pharmaceutical composition useful in the methods of the invention may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See REMINGTON'S PHARMACEUTICAL SCIENCES, 18$^{th}$ Edition, (A. R. Gennaro, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the Nodal inhibitors.

In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In preferred embodiments, pharmaceutical compositions of the present invention comprise Tris buffer of about pH 7.0-8.5, or acetate buffer of about pH 4.0-5.5, and may further include sorbitol, sucrose, Tween-20 and/or a suitable substitute therefor. In certain embodiments of the invention, Nodal inhibitor compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the Nodal inhibitor product may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired Nodal inhibitor in a pharmaceutically acceptable vehicle. A particularly suitable vehicle for parenteral injection is sterile distilled water in which the Nodal inhibitor is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used to promote sustained duration in the circulation. In certain embodiments, implantable drug delivery devices may be used to introduce the desired Nodal inhibitor.

Pharmaceutical compositions of the invention can be formulated for inhalation. In these embodiments, Nodal inhibitors are advantageously formulated as a dry, inhalable powder. In preferred embodiments, Nodal inhibitor inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins.

It is also contemplated that formulations can be administered orally. Nodal inhibitors that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the Nodal inhibitor. Diluents, flavorings, low melting point waxes, vegetable oils, lubricants, suspending agents, tablet disintegrating agents, and binders may also be employed.

A pharmaceutical composition of the invention is preferably provided to comprise an effective quantity of one or a plurality of Nodal inhibitors in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving Nodal inhibitors in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g. films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al, 1983, *Biopolymers* 22:547-556), poly(2-hydroxyethyl-methacrylate) (Langer et al., 1981, *J. Biomed. Mater. Res.* 15:167-277 and Langer, 1982, *Chem. Tech.* 12:98-105), ethylene vinyl acetate (Langer et al., supra) or poly-D(-)-3-hydroxybutyric acid (European Patent Application Publication No. EP 133,988). Sustained release compositions may also include liposomes that can be prepared by any of several methods known in the art. See e.g., Eppstein et al., 1985, *Proc. Natl. Acad. Sci. USA* 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

Nodal inhibitors useful in the methods of the invention can be admixed, encapsulated, conjugated or otherwise associated with other molecules, molecule structures or mixtures of compounds, for example, liposomes, receptor targeted molecules, oral, rectal, topical or other formulations, for assisting in uptake, distribution and/or absorption in a patient, using methods that are well known in the pharmaceutical arts.

The Nodal inhibitors, including but not limited to hESC-derived Lefty, may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like.

The Nodal inhibitors, including but not limited to hESC-derived Lefty, may also be administered intratumorally, intraperitoneally, or by injection into the microenvironment surrounding the site of an excised tumor.

Alternatively, it is possible to entrap the therapeutic agents, for delivery, in microcapsules prepared, for example, by coacervation techniques or by interfacial polymerization, for example, by the use of hydroxymethyl cellulose or gelatin-microcapsules or poly(methylmethacrylate) microcapsules, respectively, or in a colloid drug delivery system, for example, liposomes, albumin, microspheres, microemulsions, nanoparticles, nanocapsules, or in macroemulsions. Such teachings are disclosed in Remington's Pharmaceutical Sciences (1980), herein incorporated by reference.

In certain embodiments, Lefty may be administered to a patient in need thereof through the use of gene therapy, i.e. the administration of nucleic acids encoding the Lefty polypeptides. In gene therapy applications, genes are introduced into cells in order to achieve in vivo synthesis of a therapeutically effective genetic product. "Gene therapy" includes both conventional gene therapy where a lasting effect is achieved by a single treatment, and the administration of gene therapeutic agents, which involves the one time or repeated administration of a therapeutically effective DNA or mRNA.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative, flavoring and/or coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The Nodal inhibitors may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nodal inhibitors may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The formulations can also be preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

For therapeutic purposes, the Nodal inhibitors of this invention are ordinarily combined with one or more adjuvants appropriate to the indicated route of administration. If administered by mouth, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0.5 mg to about 14 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be preferable to apply a topical preparation of compounds of this invention to the affected area two to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water.

Dosing frequency will depend upon the pharmacokinetic parameters of the particular Nodal inhibitor used in the formulation. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data. In certain embodiments, Nodal inhibitors can be administered to patients throughout an extended time period.

Pharmaceutical compositions and/or Nodal inhibitors can be administered alone or in combination with other therapeutic agents, in particular, in combination with other chemotherapeutic agents.

In addition, the invention provides methods for monitoring the effectiveness of a pharmaceutical composition as an agent for treating aggressive melanoma in a patient comprising the steps of: (a) obtaining a sample of skin cells from a patient; (b) assaying the skin cells for the presence of Nodal; (c) administering an amount a pharmaceutical composition to the patient; (d) repeating step (a) using a subsequently-collected biological sample obtained from the patient; and (e) comparing the amount of Nodal detected in the skin cells from step (a) with the amount of Nodal detected in the skin cells from step (c), wherein the effectiveness of the pharmaceutical composition is monitored by detecting changes in the amount of Nodal in the subsequently-collected skin cells compared with the skin cells taken in step (a).

Unless otherwise required by context, singular terms used herein shall include pluralities and plural terms shall include the singular.

EXAMPLES

The following examples, including the experiments conducted and results achieved are provided for illustrative purposes only and are not to be construed as limiting the invention.

Example 1

Figure 2:
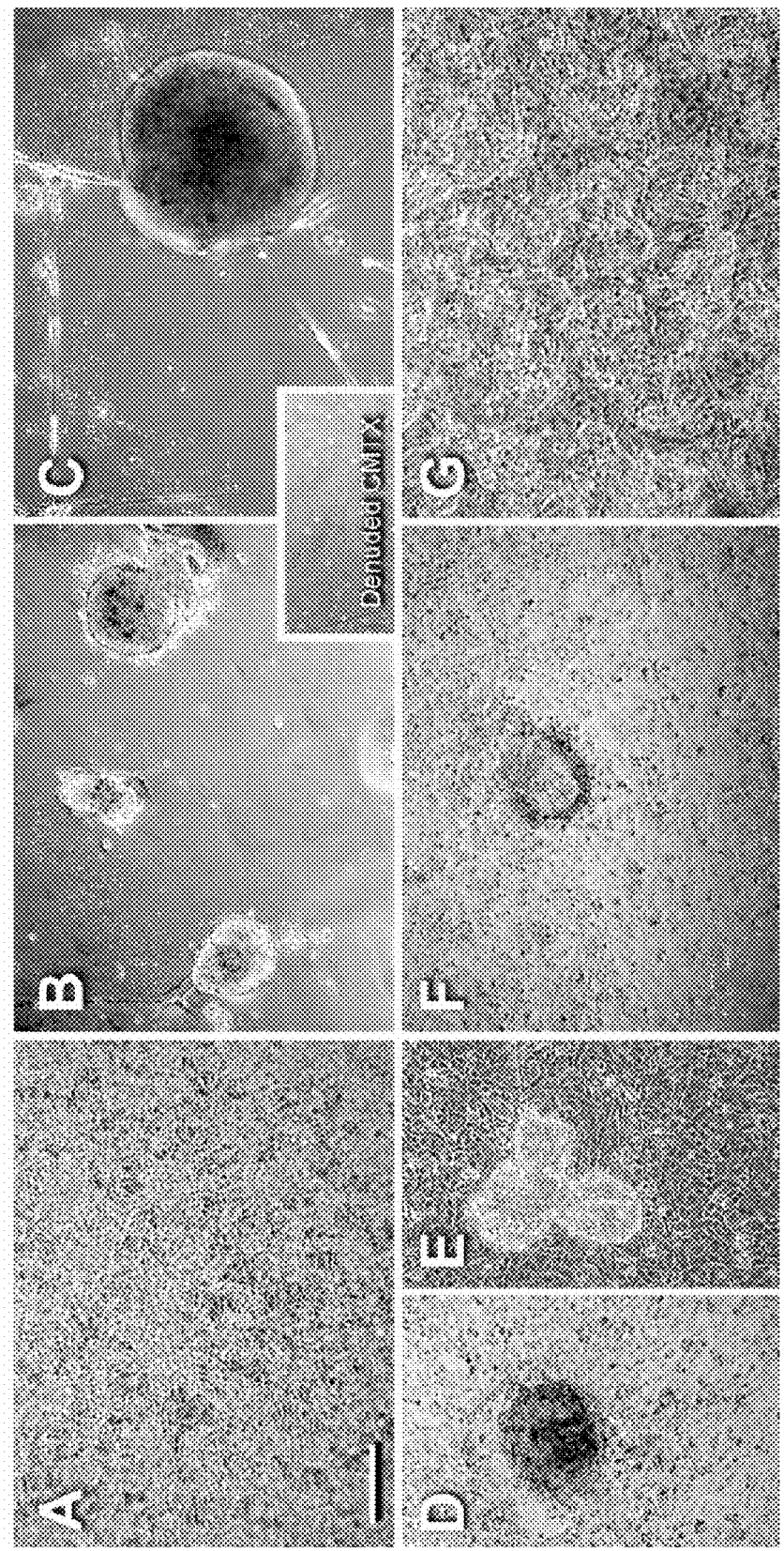
FIG. 2 shows that the microenvironment of human embryonic stem cells induces melanoma cell spheroid formation. (A-G) Phase contrast microscopy showing the confluent growth of C8161 amelanotic, human metastatic cutaneous melanoma cells on 3-D Matrigel matrix (A), compared with the formation of colonies by H1 (B) and HSF-6 (C) human embryonic stem cells (hESCs) on 3-D Matrigel matrix; following removal of the hESCs from their 3-D matrix (leaving a denuded preconditioned matrix, CMTX, shown in inset), the C8161 tumor cells seeded onto the H1 (D,E) and HSF-6 (F) hESC preconditioned matrices, CMTX (Matrigel), now form spheroids (D-F) similar to hESC colonies. (Bar in "A" equals 200 µm). In contrast, C8161 cells exposed to medium conditioned by H1 cells are unable to form spheroids (G).

3-D Matrices Preconditioned by Human Embryonic Stem Cells Promote Epigenetic Changes in Aggressive Tumor Cells As illustrated in FIG. 1, H1 or HSF-6 human embryonic stem cells (hESCs), $5 \times 10^4$ cells in compact colonies, were seeded onto a 3-D matrix comprised of growth factor-reduced Matrigel (BD Biosciences) in the presence of conditioned stem cell medium for 3 to 4 days. Subsequently, the hESCs were removed from their 3-D matrix with $NH_4OH$ followed by thorough washes with double-distilled $H_2O$, PBS, and complete medium, leaving a denuded, preconditioned, 3-D matrix (CMTX Matrigel). Onto this preconditioned matrix were seeded human amelanotic metastatic cutaneous melanoma cells (C8161), $2.5 \times 10^5$ cells/6-well dish, for 3 to 4 days. At the end of this incubation period, analyses of potential changes in morphology, gene and protein expression, and behavioral function(s) were performed on the melanoma cells exposed to the hESC preconditioned matrix microenvironment. Preconditioning of an extracellular matrix exerted a dramatic effect on melanoma cell morphology (shown in FIG. 2). On a control unconditioned Matrigel matrix, C8161 melanoma cells (FIG. 2A) grew into overconfluent monolayers, whereas undifferentiated H1 (FIG. 2B) and HSF-6 (FIG. 2C) human embryonic stem cells (hESCs) formed compact colonies of cells with a high nucleus-to-cytoplasm ratio. However, C8161 melanoma cells seeded onto the 3-D matrices preconditioned by the human embryonic stem cells acquired an altered phenotype manifested by the formation of spheroids similar to the colonies formed by human embryonic stem cells (FIG. 2D-F). In contrast, the conditioned media from human embryonic stem cells did not exert an epigenetic change on the C8161 cells (FIG. 2G), suggesting that hESCs influence melanoma cell phenotype through the alteration of the immediate microenvironment.

Figure 3:
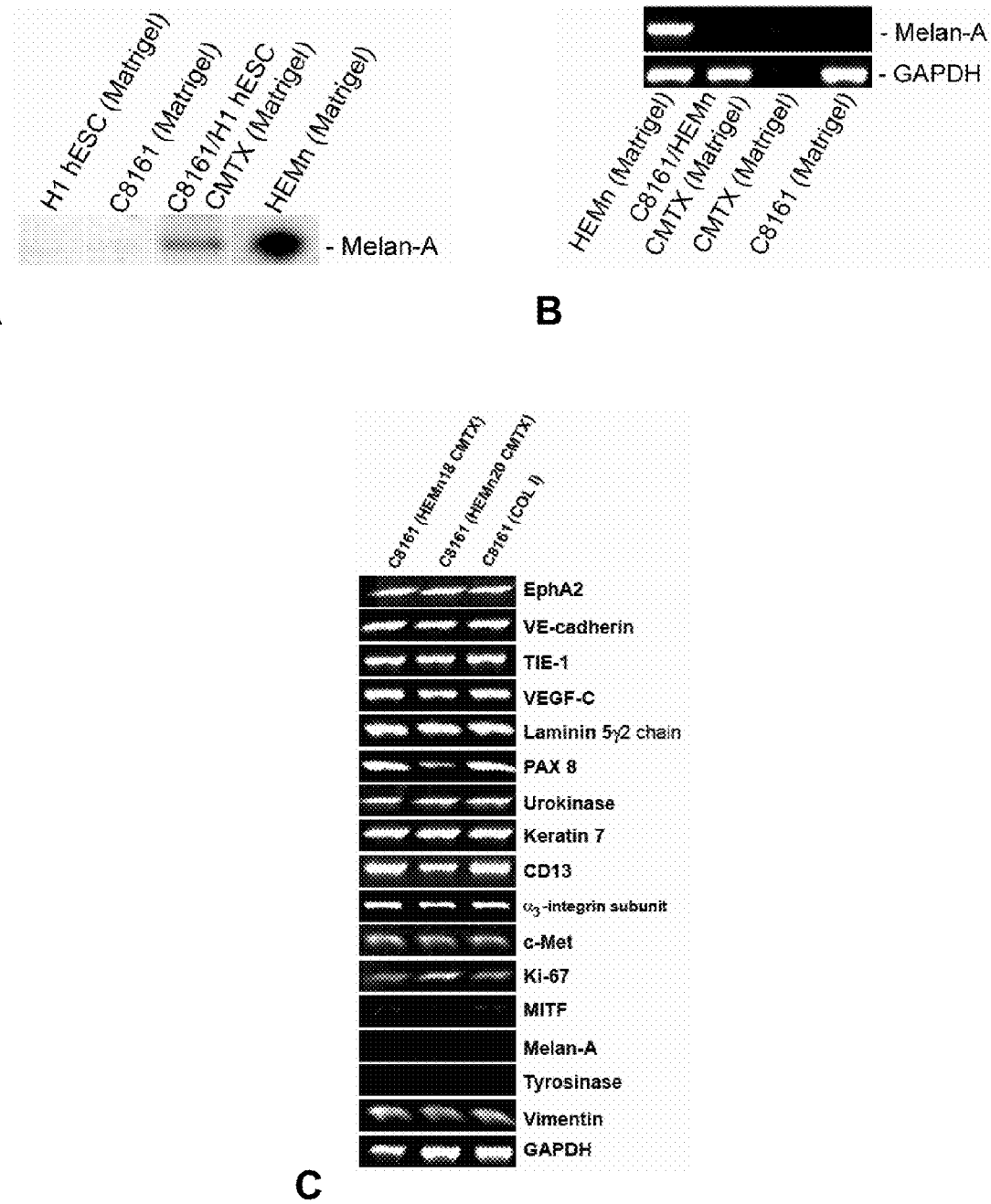
FIG. 3 shows the epigenetic changes in human metastatic cutaneous melanoma cells exposed to the microenvironment of human embryonic stem cells. (A) Western blot analysis of whole cell lysates (with an equal amount of protein loaded per sample), for a melanocyte marker, Melan-A, shows its absence in H1 hESCs on Matrigel and C8161 tumor cells on Matrigel; and the induction of Melan-A in C8161 cells exposed to the H1 hESCs preconditioned matrix, CMTX (Matrigel), compared with Melan-A in control human epidermal melanocytes (HEMn) on Matrigel (upper panel). (B) Semi-quantitative RT-PCR analysis of Melan-A gene expression in HEMn cultured on Matrigel compared to C8161 cells exposed to a HEMN preconditioned matrix, CMTX (Matrigel), compared with C8161 cells on Matrigel. The CMTX lane serves as a control demonstrating the complete removal of the HEMn cells from the preconditioned matrix prior to seeding the C8161 melanoma cells. GAPDH was used as a loading control for RNA (lower panel). (C) Semi-quantitative RT-PCR analysis demonstrating that a collagen I 3-D matrix preconditioned by human melanocytes (HEMn18 or HEMn20 CMTX) does not change the expression of the genes tested. This indicates that the benign melanocyte microenvironment does not epigenetically influence metastatic melanoma cells to change their plastic, molecular phenotype.

To further analyze epigenetic changes in the phenotype of C8161 cells exposed to the human embryonic stem cell microenvironment, Western blot and RT-PCR analyses of a melanocyte marker, Melan-A were performed (FIGS. 3A and 3B). Melan-A was absent both in H1 human embryonic stem cells (indicating their lack of a differentiated pigment cell phenotype) and in C8161 melanoma cells (illustrating their dedifferentiated phenotype) on Matrigel. However, Melan-A expression was induced in amelanotic C8161 melanoma cells exposed to the H1 preconditioned Matrigel matrix (FIG. 3A), demonstrating the epigenetic induction of a melanocyte-specific phenotype marker, similar to control melanocytes (HEMn) on Matrigel. By contrast, C8161 melanoma cells exposed to 3-D matrices preconditioned by normal HEMn were not induced to change their morphology or to express Melan-A (FIG. 3B). Thus, the normal melanocyte microenvironment does not share the ability of the hESC microenvironment to epigenetically reprogram metastatic melanoma cells to express a melanocyte-like phenotype. This was confirmed by the results of FIG. 3C, showing semi-quantitative RT-PCR analysis which demonstrates that a collagen I 3-D matrix preconditioned by human melanocytes (HEMn18 or HEMn20 CMTX) does not change the expression of the genes tested, indicating that the benign melanocyte microenvironment does not epigenetically influence metastatic melanoma cells to change their plastic, molecular phenotype.

Example 2

Figure 4:
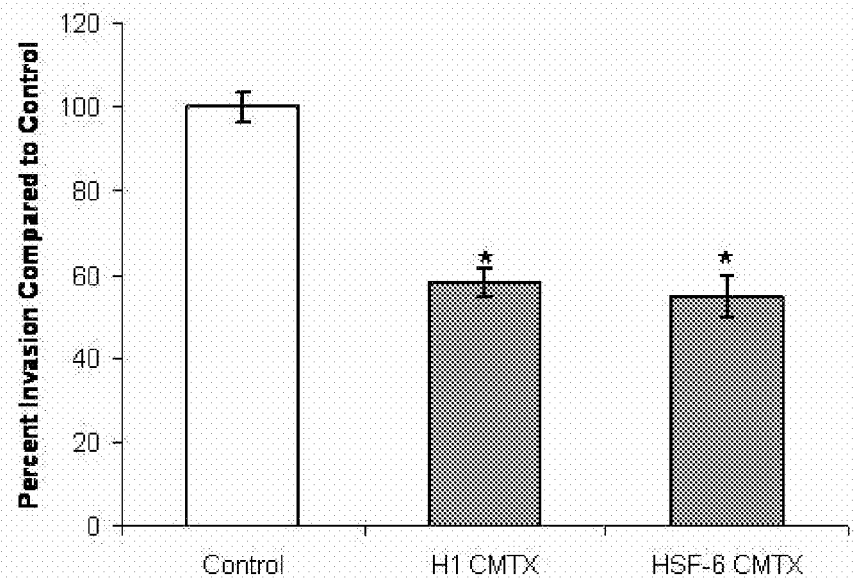
FIG. 4 shows that the microenvironment of human embryonic stem cells decreases melanoma cell invasion and tumorigenesis. (A) Invasion of C8161 cells following culture on unconditioned Matrigel (Control) or Matrigel preconditioned by either H1 or HSF-6 hESCs was calculated as a percentage of cells able to invade through a defined matrix (collagen IV, laminin, and gelatin)-coated membrane during a 24 hour period using the MICS (Membrane Invasion Culture System) assay. Bars represent the mean, normalized, invasion indices±standard deviations. The values indicated by an asterisk (*) are significantly different from the invasion index of control cells. (B) In vivo tumor formation in a mouse injected with C8161 cells pre-exposed for 3 days to either a control matrix (Matrigel) or a matrix conditioned by hESCs (H9 CMTX) (n=21). Values represent the median tumor volume (mm3)±interquartile range, and tumor volumes were significantly different at the time points indicated by an asterisk (*) (P<0.05).
Figure 4:
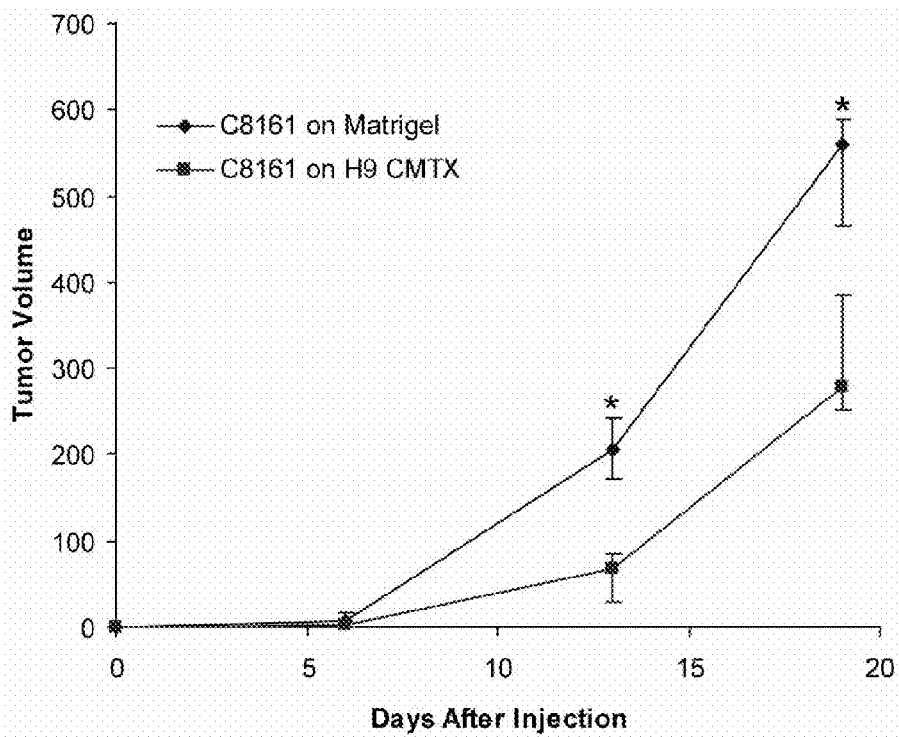

Aggressive Tumor Cells are Less Invasive and Tumorigenic Following Culture on hESC Microenvironments The aggressiveness of tumor cells is correlated with their ability to invade through the extracellular matrix; thus, the effect of hESC microenvironments on melanoma cell invasion was investigated. As illustrated in FIG. 4A, the in vitro invasiveness of aggressive C8161 cells was significantly inhibited following culture on matrices preconditioned by hESCs, suggesting suppressive, anti-invasion cues associated with this human embryonic microenvironment.

Comparable results were found in vivo tumor formation. A microenvironment of human embryonic stem cells (H9 CMTX) was prepared as described above. C8161 human cutaneous melanoma cells were exposed to the H9 CMTX or Matrigel for 3 to 4 days prior to transplantation in a mouse model. Nude immunocompromised mice received an injection of the C8161 cells subcutaneously into the midscapular region (to mimic spontaneous metastatic dissemination found in human cancers). The animals were injected using a 25 or 27-gauge needle with $2.5 \times 10^5$ tumor cells/mouse in 0.05 ml RPMI media.

Tumor size was monitored on alternate days and was measured using a microcaliper. At the time of necropsy (19 days after injection), the mice were euthanized using $CO_2$ compressed gas asphyxiation followed by cervical dislocation and the tumor and major organs were removed and prepared for histology. The sections were stained with anti-Nodal antibodies (R&D Systems) to determine Nodal expression in the tumors (see Example 6). As shown in FIGS. 4A and 4B, melanoma cells were less invasive and tumorigenic in vivo following culture on hESC microenvironments.

Example 3

Figure 5:
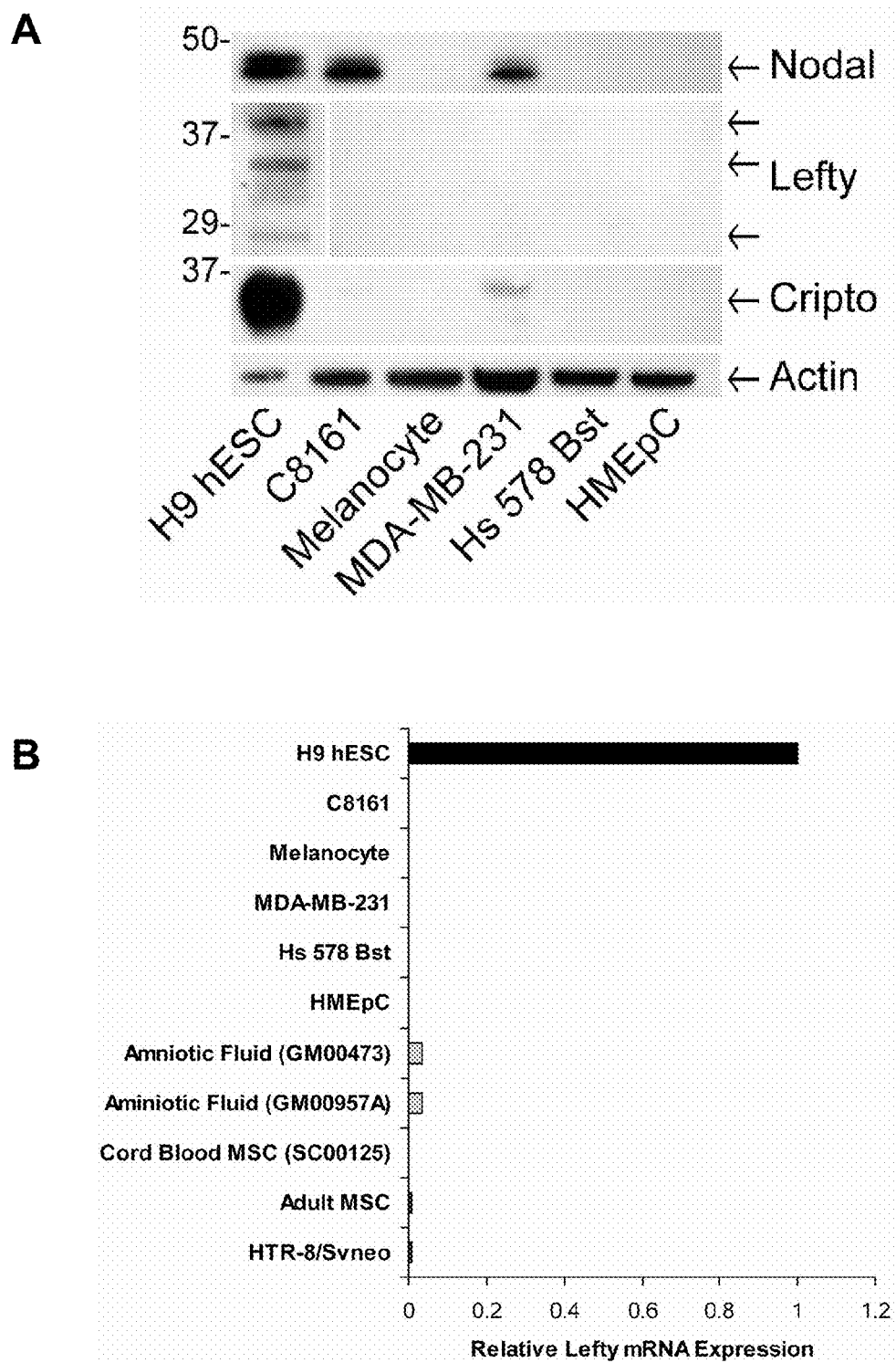
FIG. 5 shows differential expression of Nodal, Lefty, and Cripto in hESCs, aggressive tumor cells, and normal human cells. (A) Western blot analyses of Nodal, Lefty and Cripto in: H1 and H9, human embryonic stem cell (hESC) lines; C8161, human metastatic melanoma cells; normal human melanocytes; MDA-MB-231, human metastatic breast carcinoma cells; Hs 578 Bst normal human myoepithelial cells; and HMEpC normal human mammary epithelial cells. Actin is used as a loading control. (B) Real Time RT-PCR analysis of Lefty-B mRNA expression in H9, human embryonic stem cells (hESCs); C8161, human metastatic melanoma cells; normal human melanocytes; MDA-MB-231, human metastatic breast carcinoma cells; Hs 578 Bst normal human myoepithelial cells; HMEpC normal human mammary epithelial cells; GM00473 and GM00957A human amniotic fluid-derived stem cells; SC00125, human umbilical cord-derived stem cells; human adult mesenchymal stem cells (MSC); and HTR-8/SVneo, immortalized human cytotrophoblast cells. (C) Immunofluorescence localization of Cripto in 100% of H9 hESCs and in small subpopulations of C8161 melanoma and MDA-MB-231 breast carcinoma cells. Bar equals 10 µm. (D) Western blot analyses of Nodal, Lefty and Cripto in: H9, hESCs; GM00473 and GM00957A human amniotic fluid-derived stem cells; SC00125, human umbilical cord-derived stem cells; human adult mesenchymal stem cells (MSC); and HTR-8/SVneo, immortalized human cytotrophoblast cells. Actin is used as a loading control.

Characterization of Nodal Signaling Pathway Members in Human Normal Cells, Metastatic Cancer Cells, Human Embryonic Stem Cells and Other Stem Cell Types: Aggressive Tumors Express Nodal but not Lefty In order to elucidate the expression of key components of the Nodal signaling pathway in normal, neoplastic and stem cell types, Western blot analyses were conducted which revealed that in a manner similar to hESCs, metastatic melanoma (C8161) and breast carcinoma (MDA-MB-231) cells express Nodal protein at approximately 48 kDA (FIG. 5A). This is in contrast to corresponding normal cell types [melanocytes, myoepethial cells (Hs 578 Bst) and primary human mammary epithelial cells (HMEpC)], in which Nodal was not detected.

The Lefty proteins (Lefty-A, Lefty-B), divergent members of the TGF-β superfamily, spatially and temporally antagonize Nodal in embryological systems (Tabibzadeh et al., 2006, *Stem Cells* 24:1998-2006). Moreover, the Lefty genes are downstream targets of Nodal signaling, thereby providing a powerful negative-feedback loop for this pathway. Id. Using Western blot analysis it was determined that hESCs express Lefty protein at approximately 42, 34 and 28 kDAs. In contrast, Lefty is not expressed by metastatic breast carcinoma and melanoma cells or by corresponding normal somatic cell types (FIG. 5A). Real time RT-PCR analysis confirmed these results as Lefty mRNA expression was exclusive to the hESC cell lines (FIG. 5B).

Nodal propagates its signal by binding to heterodimeric complexes between type I (ALK 4/7) and type II (ActRIIB) activin-like kinase receptors. Genetic studies in zebrafish and mice have determined that Cripto, an Epidermal Growth Factor-Cripto-1/FRL1/cryptic (EGF-CFC) family member, directly associates with ALK 4 and Nodal and that these associations facilitate the ability of Nodal to propagate its signal (Schier et al.; Yeo et. al., 2001, *Mol Cell* 7:949-957). Using Western blot analysis and immunofluorescence microscopy, it was determined that hESCs uniformly express high levels of Cripto at approximately 35 kDA; however, only a subpopulation of metastatic human melanoma (C8161) and breast carcinoma (MDA-MB-231) cells express a relatively low level of Cripto (FIG. 5A,C).

In order to analyze the expression of Nodal, Lefty and Cripto in other human stem cell types and in first trimester human cytotrophoblast cells (HTR-8/SVneo), Western blot analyses were conducted which revealed that umbilical cord derived mesenchymal stem cells (MSC; SC00125) and adult MSCs do not express Nodal and Cripto, and that although amniotic fluid-derived stem cells (GM00473, GM00957A) and cytotrophoblast cells express Cripto, only the latter developmental cell type expresses an appreciable amount of Nodal (FIG. 5D). Of note, in contrast to hESCs, none of the other stem cell lines examined expressed an appreciable level of Lefty protein or mRNA (FIG. 5B).

In summary, like hESCs, cancer cells express Nodal, while unlike hESCs, they do not express Lefty. C8161 cells (human metastatic melanoma cells) and MDA-MB-231 cells (human metastatic breast carcinoma cells) expressed Nodal and Cripto (at a low level), and they did not express Lefty. Expression of Nodal, Lefty, and Cripto was undetectable in normal human melanocytes, Hs 578 Bst normal human myoepithelial cells, and HMEpC normal human mammary epithelial cells.

Example 4

Nodal Expression Correlates with Tumor Progression

Human melanoma specimens were screened for the presence of Nodal protein. Formalin-fixed, paraffin-embedded archival tissue was obtained from patients with primary or metastatic cutaneous melanoma (Loyola University Chicago, Ill.). Immunohistochemical staining was performed on a HNS 710i Automated Immunostainer (Richard-Allan Scientific (RAS), Kalamazoo, Mich.) with the Multi-Species HRP/AEC Detection Systems. Following deparaffinization in xylene, ethanol degradation, and antigen retrieval with citrate buffer, four blocking steps were applied: 0.03% hydrogen peroxide, Avidin and Biotin blocks (Avidin/Biotin blocking kit, Vector Laboratories, Inc., Burlingame, Calif.), and a Serum-Free protein block. Anti-Nodal antibody (20 μg/mL, R&D) was applied for 90 minutes. Slides were rinsed in TBS-T, incubated with biotinylated anti-goat IgG (2 μg/ml, Vector Labs), washed with TBS-T and incubated with the streptavidin peroxidase reagent for 15 minutes. Color was produced with AEC (red) substrate (RAS) and counterstaining with Mayer's hematoxylin. Samples were dehydrated in reagent grade alcohol and cover slipped with permanent mounting medium. Negative control reactions were conducted with ChromPure Goat IgG (Jackson Labs), isotype matched and used at the same concentration as the Nodal antibody.

Figure 6:
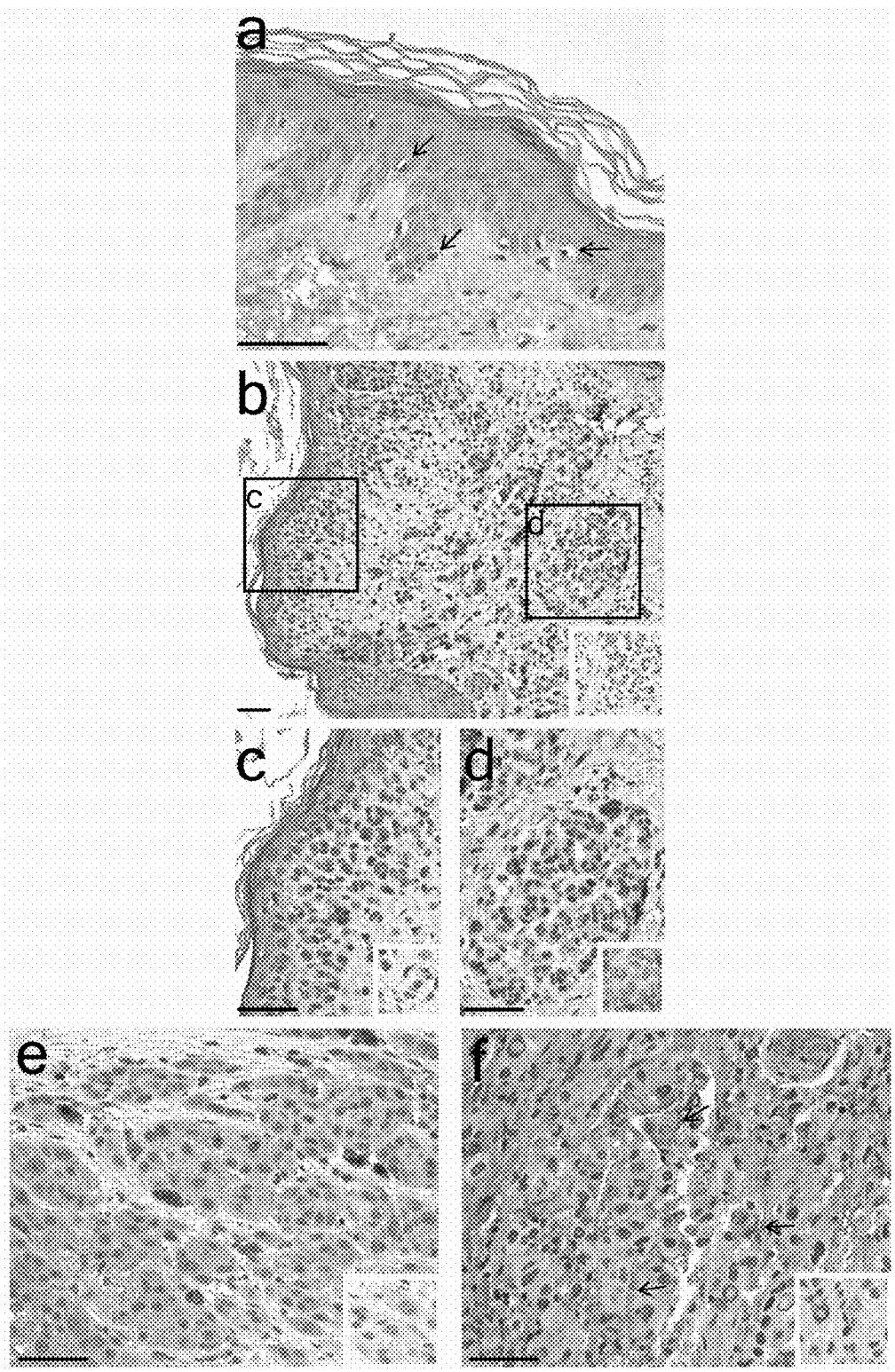
FIG. 6 shows patterns of Nodal Expression in Primary and Metastatic Melanoma Lesions.
Figure 10:
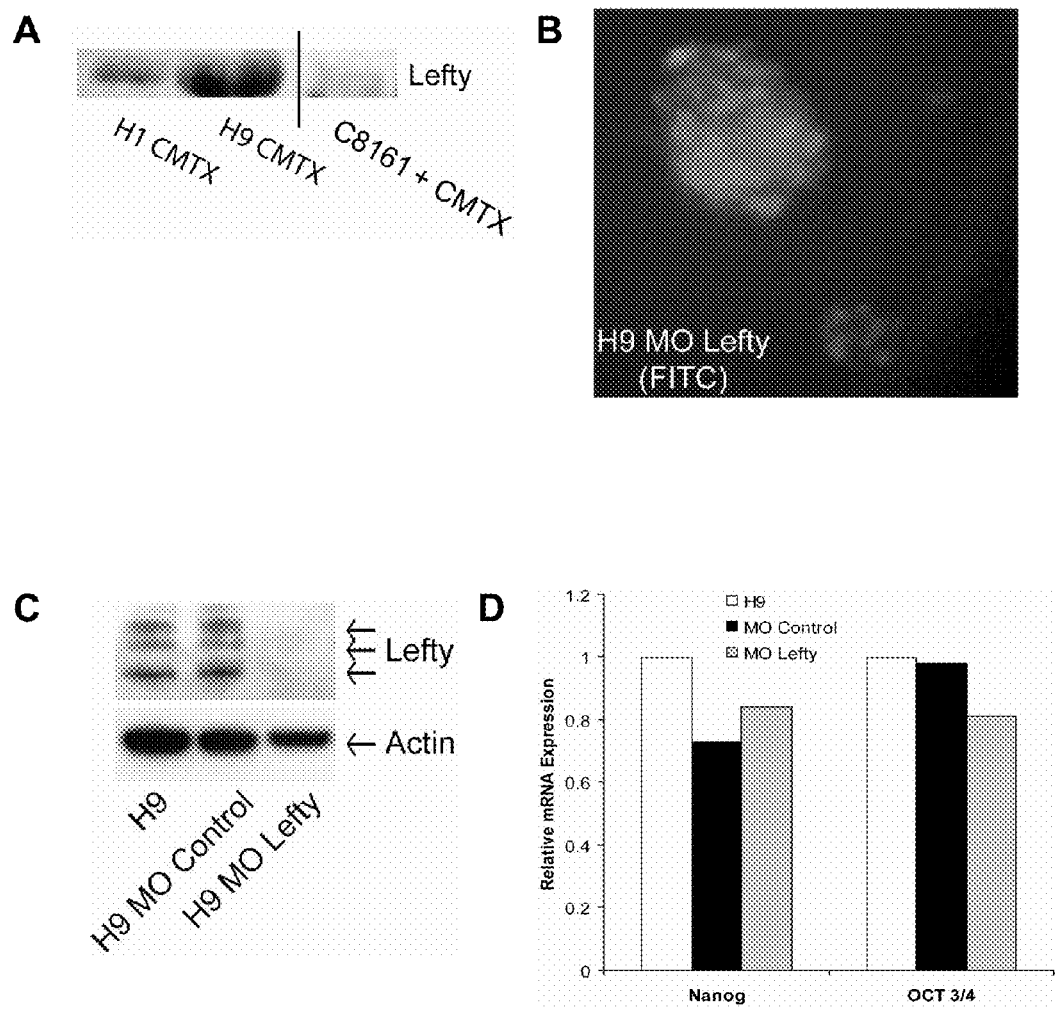
FIG. 10 shows the role of hESC-derived Lefty in Nodal down-regulation. (A) An abundance of the Nodal inhibitor Lefty within the hESC conditioned matrices (CMTX). Lefty protein is absent in the C8161 cells within its own conditioned matrix (C8161+CMTX). (B) Immunofluorescence localization of FITC-conjugated anti Lefty Morpholinos ($MO^{LEFTY}$) in H9 hESC colonies on Matrigel. (C) Western blot analysis of Lefty protein in H9 hESCs treated with either vehicle (Control), $MO^{Control}$ (MO Control), or $MO^{Lefty}$ (MO Lefty). Actin is used as a loading control. (D) Real Time RT-PCR analysis of Oct-3/4 and Nanog expression in H9 hESCs treated with either vehicle (H9), $MO^{CONTROL}$ (MO Control), or $MO^{LEFTY}$ (MO Lefty). Gene levels were normalized using 18s and bars represent mean gene expression normalized to H9. (E) Real Time RT-PCR analysis of Nodal mRNA expression in C8161 cells cultured for 3 days on control (unconditioned) Matrigel, Matrigel conditioned by hESCs (H9 CMTX) or Matrigel conditioned by hESCs in which Lefty protein expression was knocked out with Lefty-specific Morpholinos (H9 CMTX MO Lefty). (F) Western blot analysis of Nodal protein in human metastatic melanoma (C8161) and breast carcinoma (MDA-MB-231) cells exposed for 3 days to either control (unconditioned) Matrigel or to Matrigel seeded with Lefty protein purified from hESCs (H9-derived Lefty). MDA-MB-231 cells were allowed to recover on fresh Matrigel for 2 days prior to analysis and Actin is used as a loading control. (G) Relative colony formation of C8161 and MDA-MB-231 cells cultured on soft agar for 14 days following 3 days of exposure to either control Matrigel or Matrigel seeded with Lefty purified from hESCs (Lefty), in the presence or absence of rNodal (100 ng/mL). Bars represent mean normalized colony formation±standard deviation. The values indicated by an asterisk (*) are significantly different from the colony forming ability of control cells (n=6, P<0.05).

The immunohistochemistry demonstrated that Nodal is absent in normal skin (FIG. 6A) and is weakly expressed or absent in primary melanomas (FIG. 6B). In the primary lesions, Nodal immunostaining was generally confined to small clusters of tumor cells in the vertical growth phase and was rarely observed in radial lesions (n=5; FIGS. 6C and D). In contrast, Nodal protein was expressed in 60% of the cutaneous melanoma metastases examined (n=10; FIGS. 6E and F). Immunostaining was heterogeneous, varying among patients in extent, intensity and localization. For example, Nodal was found localized to cell membranes, and was expressed diffusely in the cytoplasm (FIG. 10). Western blot analyses similarly revealed that 45% of metastatic melanomas tested were positive for Nodal (n=22). This is in contrast to normal skin (n=9), and melanocytes (n=5); neither of which expressed Nodal (data summarized in Table 1). Collectively, these results demonstrated that Nodal expression was positively correlated with melanoma progression.

TABLE 1

|  | Nodal Staining (IHC) | Case Type | Nodal Signal (Western) |
| --- | --- | --- | --- |
|  |  | Normal Skin | – |
|  |  | Normal Skin | – |
|  |  | Normal Skin | – |
|  |  | Normal Skin | – |
| Primary | – | Normal Skin | – |
| Primary | – | Normal Skin | – |
| Primary | –* | Normal Skin | – |
| Primary | –* | Normal Skin | – |
| Primary | –* | Normal Skin | – |
| Metastasis | –* | Melanocytes | – |
| Metastasis | ++ | Melanocytes | – |
| Metastasis | + | Melanocytes | – |
| Metastasis | + | Melanocytes | – |
| Metastasis | – | Melanocytes | – |
| Metastasis | – | Dendritic Cells | – |
| Metastasis | – | Dendritic Cells | – |
| Metastasis | ++ | Metastatic Melanoma | – |
| Metastasis | ++ | Metastatic Melanoma | – |
| Metastasis | ++ | Metastatic Melanoma | + |
|  |  | Metastatic Melanoma | + |
|  |  | Metastatic Melanoma | – |
|  |  | Metastatic Melanoma | – |
|  |  | Metastatic Melanoma | – |
|  |  | Metastatic Melanoma | + |
|  |  | Metastatic Melanoma | – |
|  |  | Metastatic Melanoma | – |
|  |  | Metastatic Melanoma | + |
|  |  | Metastatic Melanoma | – |
|  |  | Metastatic Melanoma | + |
|  |  | Metastatic Melanoma | – |
|  |  | Metastatic Melanoma | – |
|  |  | Metastatic Melanoma | + |
|  |  | Metastatic Melanoma | – |
|  |  | Metastatic Melanoma | + |
|  |  | Metastatic Melanoma | + |
|  |  | Metastatic Melanoma | + |

TABLE 1-continued

|  | Nodal Staining (IHC) | Case Type | Nodal Signal (Western) |
| --- | --- | --- | --- |
|  |  | Metastatic Melanoma | – |
|  |  | Metastatic Melanoma | + |

Figure 7:
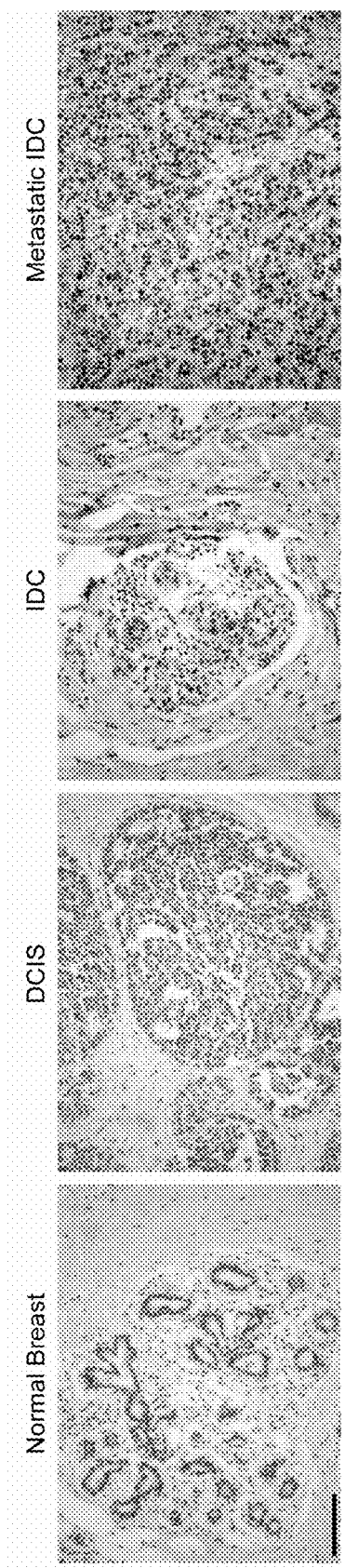
FIG. 7 shows patterns of Nodal Expression in Breast Cancer Carcinoma. Immunohistochemical analysis of Nodal staining in normal breast tissue, ductal carcinoma in situ (DCIS), invasive ductal carcinoma (IDC) and metastatic IDC. Bars equal 100 m.

++ Represents strong positive staining for Nodal encompassing >75% of the tumor mass
+ Represents positive staining for Nodal encompassing >50% of the tumor mass or the detection of Nodal using Western Blot analyses
–* Represents Nodal staining in a small subpopulation (<10%) of the tumor mass
– Represents the absence of Nodal As with the positive correlation of Nodal expression with melanoma progression, such that Nodal protein is not expressed in normal melanocytes or radial growth phase melanomas, but is present in more aggressive vertical growth phase and metastatic lesions, immunohistochemical analysis of a human breast tissue microarray (TMA) revealed that Nodal protein is similarly absent in normal breast tissue, and that its expression is positively correlated with breast carcinoma progression (FIG. 7).

The expression and prevalence of Nodal staining in breast tissue was designated as none, weak (<25%), moderate (25-75%) or strong (>75%). DCIS is ductal carcinoma in situ and IDC is invasive ductal carcinoma. Spearman's rank correlation showed a significant positive correlation between breast cancer progression and Nodal expression (P<0.05) (data summarized in Table 2).

TABLE 2

|  | None | Weak | Moderate | Strong | Total |
| --- | --- | --- | --- | --- | --- |
| Benign | 26 | 1 | 0 | 0 | 27 |
| DCIS | 3 | 0 | 0 | 0 | 3 |
| IDC | 24 | 1 | 3 | 5 | 33 |

Example 5

Localization of Nodal and Lefty in hESC Matrices

Figure 8:
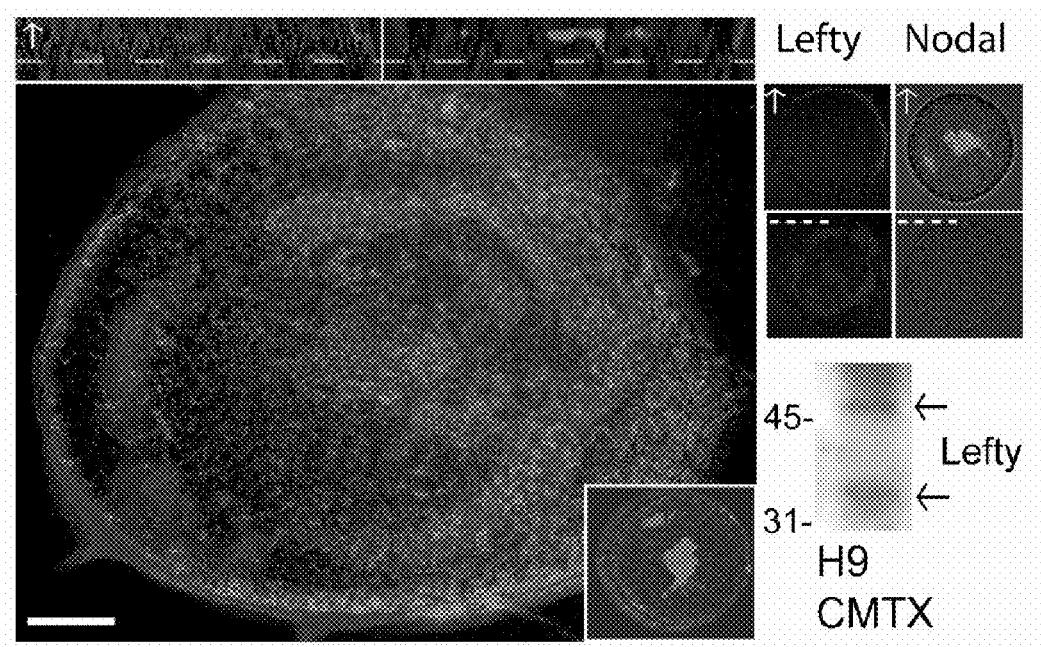
FIG. 8 shows the distribution of Nodal and Lefty on hESCs cultured on Matrigel. Immunofluorescence localization of Lefty and Nodal in H9 hESCs cultured on Matrigel and Western blot analysis of Lefty protein in matrix conditioned by hESCs (H9 CMTX). Top panels represent reconstructed confocal images depicting the cross-section of a hESC colony with its underlying matrix. Dashed line designates the cell-matrix interface and the arrow points to the upper surface of the hESC colony. Corresponding images on the right illustrate Lefty and Nodal at the cell surface (arrow) and the cell-matrix interface (dashed line). The large image is a 3-dimensional confocal projection of hESC colonies stained with Lefty and Nodal (inset). Bar equals 25 μm.

Immunofluorescence localization with confocal microscopy was performed in order to visualize the deposition of Lefty into the microenvironment of hESCs. Utilizing this methodology, it was determined that Lefty protein localizes to the areas where hESCs are in contact with the underlying Matrigel matrix, and that hESC-derived Lefty permeates into the underlying matrix (FIG. 8). This is in contrast to Nodal protein, which localizes to the surface of hESC colonies. These results were confirmed with Western blot analyses, which demonstrated that Lefty protein can be detected in Matrigel conditioned by H9 hESCs (H9 CMTX; FIG. 8), but that Nodal protein is not detectable in this H9 CMTX. Furthermore, neither Nodal nor Lefty were found in unconditioned control Matrigel alone.

Example 6

Figure 9:
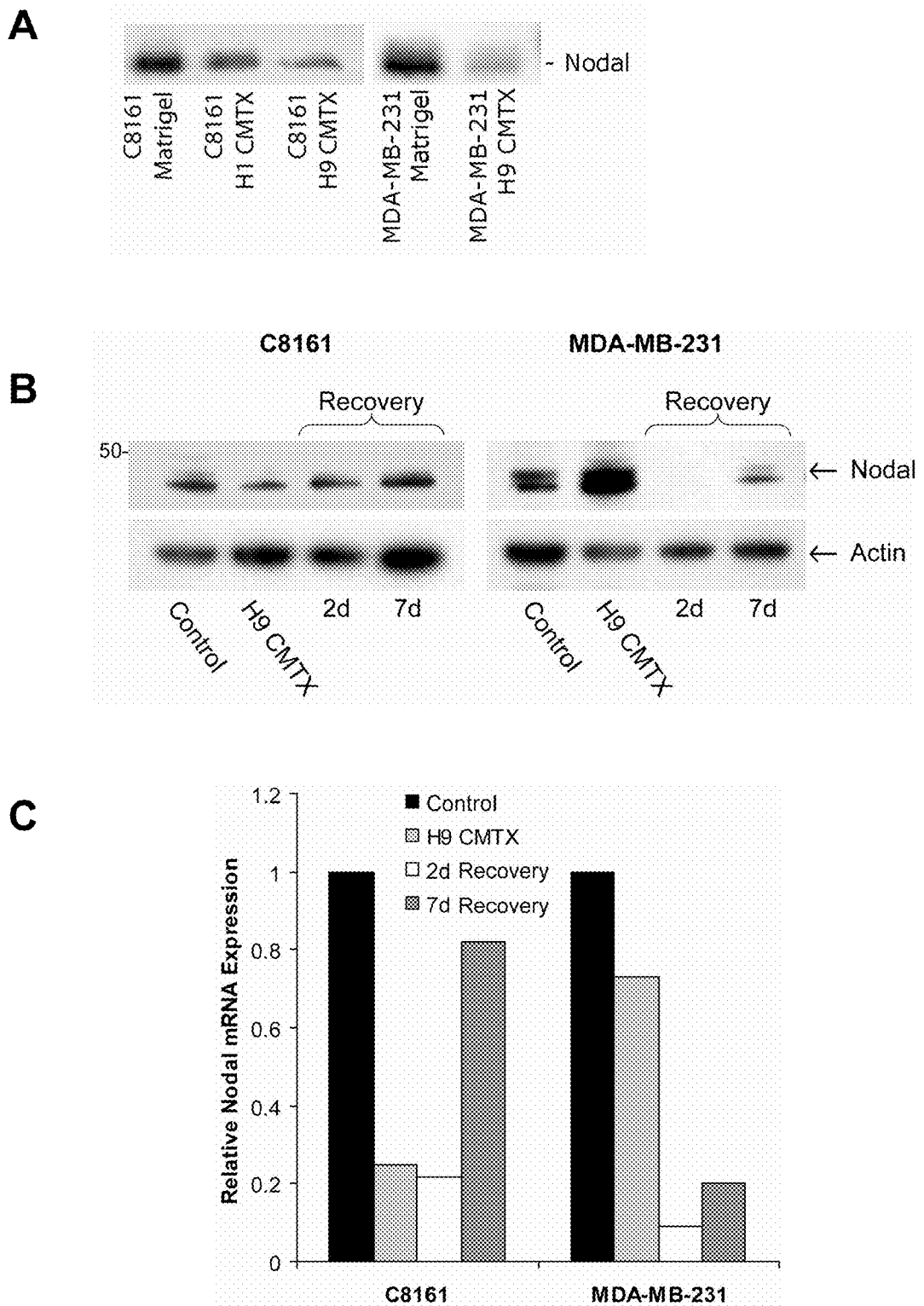
FIG. 9 shows that the microenvironment of human embryonic stem cells (hESCs) leads to the reduction of Nodal expression and tumorgenicity in plastic metastatic melanoma and breast cancer cells exposed to the embryonic preconditioned matrix. (A) Western blot analyses demonstrating that the microenvironments of hESCs reduced the expression of Nodal protein in multipotent melanoma (C8161) and breast carcinoma (MDA-MB-231) cells. (B) Western blot analyses of Nodal protein in human metastatic melanoma cells (C8161) and human metastatic breast carcinoma cells (MDA-MB-231) exposed for 3 days to either control (unconditioned) Matrigel or to Matrigel conditioned by hESCs (H9 CMTX). Some cancer cells exposed to H9 CMTX were subsequently recovered on control (unconditioned) Matrigel for 2 or 7 days prior to Western blot analysis. Actin is used as a loading control. (C) Real Time RT-PCR analysis of Nodal mRNA in human metastatic melanoma cells (C8161) and human metastatic breast carcinoma cells (MDA-MB-231) exposed for 3 days to either control (unconditioned) Matrigel or to Matrigel conditioned by hESCs (H9 CMTX). Some cancer cells exposed to H9 CMTX were subsequently recovered on control (unconditioned) Matrigel for 2 or 7 days prior to analysis. (D) Immunohistochemistry localization of Nodal in C8161 cells forming tumors in nude mice at Day 19. Nodal staining is strongest in the Matrigel control injected tumor cells vs. the diminished Nodal staining in C8161 cells exposed to the H9 CMTX (correlated with a lower tumor burden). (Bars equal 50 μm.) (E) Relative colony formation of C8161 and MDA-MB-231 cells cultured on soft agar for 14 days following 3 days of exposure to either control (unconditioned) Matrigel or to H9 CMTX. Assays were conducted in the presence or absence of rNodal (100 ng/mL). Bars represent mean normalized colony formation standard deviation. The values indicated by an asterisk (*) are significantly different from the colony forming ability of control cells and the values indicted by a double asterisk (**) are significantly different from the colony forming ability of control cells and H9 CMTX treated cells (n=12, P<0.05). (F) Western blot analyses of Nodal protein in human metastatic melanoma cells (C8161) and human metastatic breast carcinoma cells (MDA-MB-231) exposed for 3 days to either control (unconditioned) Matrigel or to Matrigel conditioned by normal melanocytes (melanocyte CMTX), normal myoepithelial cells (Hs 578 Bst CMTX), amniotic fluid-derived stem cells (GM00473/GM00957A CMTX) or trophoblast cells (HTR-8/SVneo CMTX). Actin is used as a loading control. (G) Real Time RT-PCR analysis of Nodal mRNA in human metastatic melanoma cells (C8161) exposed for 3 days to either control (unconditioned) Matrigel or to Matrigel conditioned by amniotic fluid-derived stem cells (GM 00473/GM 00957A CMTX) or trophoblast cells (HTR-8/SVneo CMTX). Gene levels were normalized using 18s and bars represent mean gene expression normalized to H9 (A,B) or Matrigel (C,D) values.

Nodal Expression Down-Regulated in Aggressive Tumor Cells Exposed to hESC Conditioned Matrix A determination of the effects of H9 CMTX on Nodal expression in metastatic melanoma (C8161) and breast carcinoma (MDA-MB-231) cells was undertaken. As illustrated in FIG. 9, the microenvironment of human embryonic stem cells (hESCs) leads to the reduction of Nodal expression and tumorgenicity in plastic metastatic melanoma and breast cancer cells exposed to the embryonic preconditioned matrix. Western blot analyses (see below) revealed that the microenvironments of hESCs reduced the expression of Nodal protein in multipotent melanoma (C8161) and breast carcinoma (MDA-MB-231) cells (FIG. 9A). Exposure to H9 CMTX down-regulates Nodal protein expression in both melanoma and breast carcinoma cells, and this effect is reversible over time (FIG. 9B). Exposure to H9 CMTX similarly abrogates Nodal mRNA expression in the melanoma and breast carcinoma cells (FIG. 9C).

FIG. 9D shows immunohistochemical analysis of Nodal staining in an orthotopic tumor derived from C8161 cells pre-exposed to Matrigel or a hESC conditioned matrix (H9 CMTX) (from in vivo experiment in Example 2). The C8161 cells exposed to the H9 CMTX expressed much less Nodal.

As a functional correlate, it was determined that exposure of C8161 and MDA-MB-231 cells to H9 CTMX results in a significant reduction in their ability to undergo anchorage independent growth, and that this inhibition of in vitro clonogenicity can be partially rescued by the inclusion of recombinant Nodal (100 ng/mL) (FIG. 9E). Of note, using Western blot analysis in conjunction with real time RT-PCR, the ability to inhibit Nodal expression in cancer cells was shown to be exclusive to the microenvironment of hESCs (FIGS. 9F & 9G). For example, exposure of C8161 cells to matrices conditioned by melanocytes, amniotic fluid derived stem cells (GM00473, GM00957A), or cytotrophoblast cells (HTR-8/SVneo) did not inhibit Nodal protein or mRNA expression (FIGS. 9F & 9G), thus illuminating the exclusivity of the epigenetic influence of the hESC microenvironment.

Western Blot Analyses

Protein lysates were prepared and quantified as previously described in Hess et al., 2001, *Cancer Res.* 61:3250-3255. Equal amounts of protein were separated by SDS-polyacrylamide gel electrophoresis under reducing conditions, and the resolved proteins were transferred onto Immobilon-P membranes (Millipore Corp., Bedford, Mass.). Membranes were blocked in 1% TBS, 0.1% Tween 20 (TBS-T) and 5% dry milk powder or 3% gelatin (for Nodal Westerns). Blots were incubated with anti-Nodal or anti-Lefty antibodies (Polyclonal rabbit anti-Nodal (H-110) 1:500 Santa Cruz Biotechnology, Santa Cruz, Calif.; Polyclonal goat anti-Lefty 1:500 R&D Systems, Minneapolis, Minn.), washed in TBS-T, and incubated with the appropriate horseradish peroxidase-labeled secondary antibody. Secondary antibodies were detected by enhanced chemiluminescence (Super Signal; Pierce, Rockford, Ill.) and exposure to autoradiography film (Molecular Technologies, St Louis, Mo.). Nodal protein was detected as two major bands at ~48 and ~35 kDa representing precursor and pro-Nodal respectively. Nodal often appeared as multiple bands, likely due to degradation of protein modifications. All experiments were done at least three times.

Example 7

Lefty is a Major hESC-Derived Factor Responsible for Inhibiting Nodal Expression and Clonogenicity in Metastatic Cancer Cells As noted previously, the microenvironment of human embryonic stem cells (hESCs) leads to the reduction of Nodal expression and tumorgenicity in plastic metastatic melanoma and breast cancer cells exposed to the embryonic preconditioned matrix. It was determined that there is an abundance of the Nodal inhibitor Lefty within the hESC conditioned matrices (FIG. 10A; CMTX). By contrast, Lefty protein was absent in the C8161 cells on its own conditioned matrix (FIG. 10A; C8161+CMTX).

Cancer cells were also exposed to Matrigel conditioned by hESCs in which Lefty protein expression was knocked down with FITC-tagged Morpholino oligonucleotides specific for Lefty-A and Lefty-B ($MO^{LEFTY}$). The fluorescently-tagged Morpholinos could be detected microscopically in over 75% of the hESC colonies treated (FIG. 10B), and Western blot analysis confirmed the efficient knock down of Lefty protein in hESCs for up to 3 days (FIG. 10C). The expression of Oct-3/4 and Nanog, representative of hESC pluripotency, was not affected during this time, and the morphology of the hESC colonies was not altered. Thus, although $MO^{LEFTY}$ efficiently knocked down Lefty protein expression in the hESCs, it did not induce stem cell differentiation (FIG. 10D). Real time RT-PCR analysis revealed that exposure of metastatic melanoma cells to Matrigel conditioned by H9 hESCs treated with $MO^{LEFTY}$ did not result in an abrogation of Nodal expression (FIG. 10E). In fact this "H9 Lefty-deficient" matrix up-regulated Nodal mRNA expression in the C8161 cells (FIG. 10E).

Additionally, Dynabeads covalently coupled to anti-Lefty antibody were utilized to isolate Lefty from hESCs cultured on a feeder-free Matrigel matrix. This purified hESC-derived Lefty was subsequently seeded into fresh Matrigel and the effects of the "Lefty-containing" matrix on cancer cell phenotype were examined. Western blot analysis revealed that hESC-derived Lefty abrogates and diminishes Nodal protein expression in metastatic melanoma (C8161) and breast carcinoma (MDA-MB-231) cells, respectively (FIG. 10F).

Also, exposure of C8161 and MDA-MB-231 cells to "H9 Lefty-containing" matrix was found to significantly reduce anchorage independent growth, and this inhibition of in vitro clonogenicity could be completely rescued by the inclusion of recombinant Nodal (100 ng/mL) (FIG. 10G).

Example 8 rLefty Capable of Inhibiting Nodal at Elevated Concentrations

Figure 11:
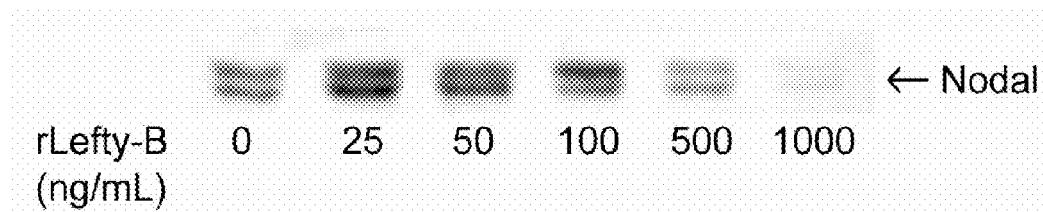
FIG. 11 shows the down-regulation of Nodal by recombinant Lefty. Western blot analysis of Nodal protein in C8161 cells exposed for 48 hrs to varying concentrations (0-1000 ng/mL) of rLefty-B showing that the addition of rLefty to C8161 cells reduces Nodal expression

As shown in the Western blot in FIG. 11, addition of rLefty to C8161 cells reduces Nodal expression at the concentrations shown. rLeftyB can inhibit Nodal protein in C8161 cells, but at a higher doses than its hESC counterpart. These results are consistent with prior findings (Tabibzadeh, S et al., 2006, *Stem Cells* 24: 1998-2006).

Example 9

Lefty Derived from hESC's, Unlike Recombinant Lefty, is Glycosylated

Figure 12:
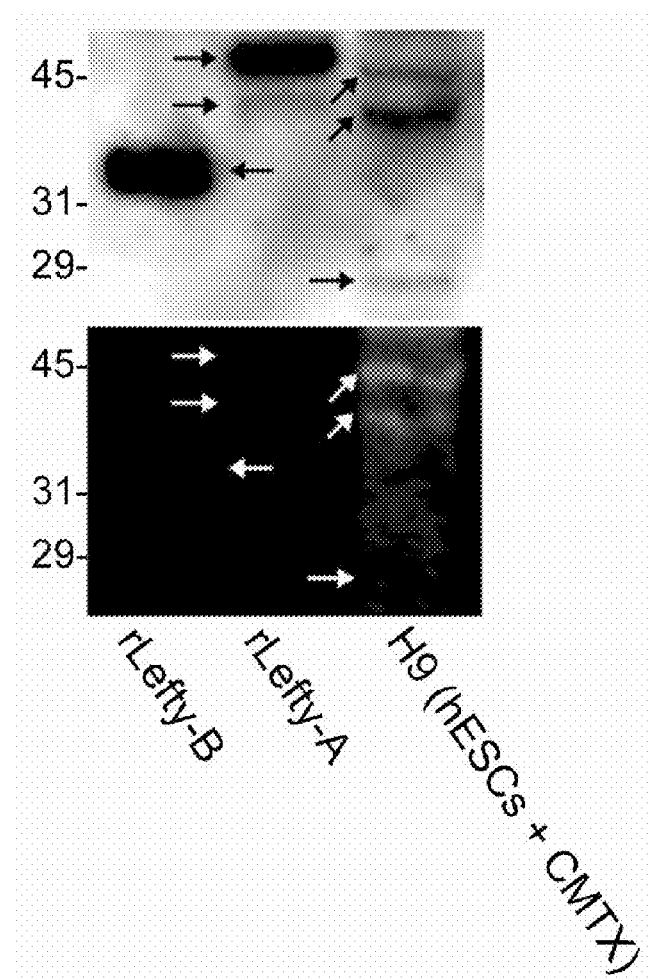
FIG. 12 shows that hESC derived Lefty is glycosylated. Staining for glycoprotein and detection of Lefty-A and Lefty-B on a Western blot containing recombinant Lefty (rLefty)-B, rLefty-A and a lysate from H9 human embryonic stem cells (hESCs) plus matrix conditioned by the H9 hESCs for 3 days (CMTX). After SDS-polyacrylamide gel electrophoresis, the proteins were transblotted and stained for glycoproteins, identified by green bands (bottom). Lefty-A and -B were subsequently detected by Western blot analysis (top). Arrows point to Lefty protein(s) on the Western blot and to the identical locations on the image showing the stained glycoproteins.

In an effort to understand the disparate results between hESC-derived Lefty and rLefty on Nodal signaling, an analysis of glycoprotein content in rLefty-B, rLefty-A and a lysate from the H9 hESCs plus their conditioned matrix was undertaking. It was found that in contrast to the rLefty proteins, H9-derived Lefty is heavily glycosylated (FIG. 12).

Example 10

Lefty Derived from hESCs Induces Apoptosis, Decreases Proliferation, and Abrogates Vasculogenic Mimicry in Aggressive Tumors In Vivo The effects of hESC derived Lefty on aggressive tumor cells were examined using an orthotopic in vivo mouse model for melanoma.

Orthotopic In Vivo Mouse Model for Melanoma: The nude mice received an injection of human cutaneous malignant melanoma cells from the established tissue culture cell line C8161 subcutaneously into the midscapular region (to mimic spontaneous metastatic dissemination found in human cancers). The animals were injected using a 25 or 27-gauge needle with $2.5 \times 10^5$ tumor cells/mouse (maximum volume of 0.1 ml in Hank's Balanced Salt Solution; HBSS) and were not handled until primary tumors were noted (usually at two weeks). Tumor size was monitored on alternate days and tumor size measured using a microcaliper on a weekly basis. At day 21, all mice in a given experiment were sacrificed using ketamine/xylazine followed by cervical dislocation and all organs removed and examined for micrometastases.

Recovery of hESC-derived Lefty protein from hESC plus CMTX: After culturing human embryonic stem cells (hESC) in six-well culture dishes on a Matrigel 3-D matrix/well for 3 days (until cells were 80% confluent), each well was washed two times with PBS, then the cells lysed with 50 μL/well of RIPA buffer (100 mM Tris/5 mM EDTA/0.15 M NaCl/1% deoxycholate/1% Triton X-100/0.1% SDS, pH 7.5) plus protease inhibitor cocktail (Complete Mini, Roche Diagnostic). The cells plus CMTX were scrapped from 12 wells and pooled into one microfuge tube, sonicated on ice using short pulses equaling a total of 2-3 seconds, centrifuged at 13,000 rpm (4° C.) for 40 minutes, and the supernatant mixed (by vortexing) with anti-Lefty antibody coated magnetic beads for 2 minutes. The sample was then mixed by rotation for 16-20 hours at 4° C. after which the magnetic beads were recovered and washed with 500 μl of 0.2M Tris, pH 8.5, and the cell-derived Lefty protein eluted from the beads using 100 μl of 0.2 M Tris/0.5 M NaCl, pH 8.5 for 1 hour at 4° C., followed by a second round of elution using the same protocol. The two sample eluates were then pooled and stored at −80° C. for subsequent analysis and use.

Administration of Lefty to the Melanoma Tumor Xenografts: After formation of palpable primary melanoma tumors (@2 weeks following orthotopic injection of C8161 cells), each tumor received subsequent intratumoral injections every 2 days over a 2 week period consisting of: hESC-derived Lefty or recombinant Lefty (rLefty; R&D Systems) or Hank's Balanced Salt Solution (HBSS) placebo. The cumulative amount of Lefty administered was @46 ng.

Immunohistochemistry for Mouse Tissue Sections: Proliferation (Ki67) and TUNEL (Apoptosis) Assays: Tissues from the orthotopic tumor models were formalin-fixed then paraffin-embedded and immunohistochemical staining on this tissue conducted using a Ki67-specific antibody for the detection of cell proliferation or normal Goat IgG (control), followed by biotinylated antibody to goat IgG, then streptavidin-conjugated peroxidase reagent. Color was produced by adding DAB substrate (red/brown) and counterstaining with Mayer hematoxylin. The TUNEL assays to measure apoptosis were conducted as per manufacturer's instructions (Millipore/Upstate). Proliferation is indicated by the presence of Ki67 staining while apoptotic nuclei were detected with confocal microscopy and are seen as red fluorescence staining localized to the nuclei of apoptotic tumor cells. For the TUNEL analyses, cell nuclei were counterstained blue with DAPI.

Periodic Acid Schiff (PAS) Staining of Vasculogenic Mimicry-Associated Networks in Tissue Sections: Tissue sections were deparaffinized, hydrated in graded ethanol then washed twice with distilled water. This was followed by 0.5% periodic acid solution for 6 minutes, two washes with distilled water, then Schiff's reagent for 5 minutes. After washes with distilled water, the samples were dehydrated with a graded series of ethanol washes, xylenes, then mounted on microscope slides with acrytol and observed with a light microscope and photographed using a green filter. The presence of PAS-positive networks (which appear grey/black) indicates the formation of extracellular matrix-rich networks formed by aggressive tumor cells—representing an extravascular perfusion pathway which we have shown to be a selective advantage for aggressive tumors in seeking a blood supply.

Figure 18:
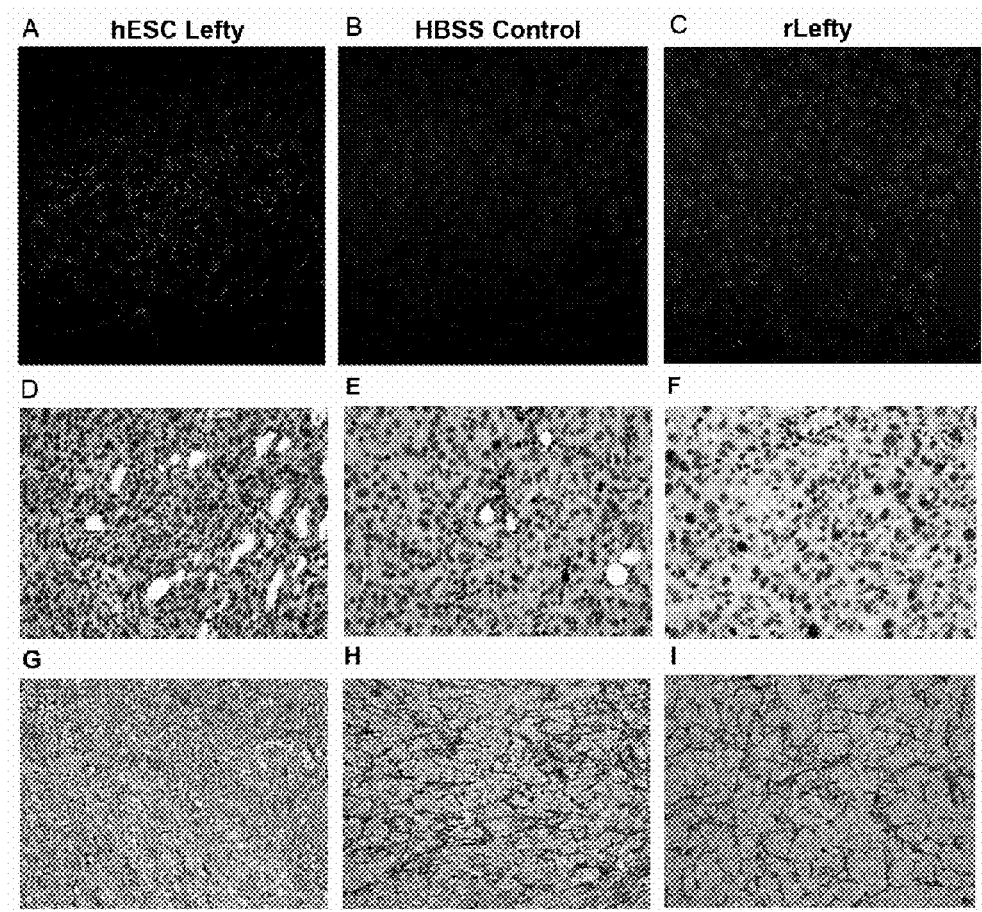
FIG. 18 shows that human embryonic stem cell-derived Lefty induces apoptosis, decreases proliferation, and abrogates vasculogenic mimicry in metastatic melanoma cells in vivo. C8161 human cutaneous metastatic melanoma cells were injected (250,000 cells/animal) orthotopically into a nude mouse model and allowed to form a palpable primary tumor mass for 2 weeks. Subsequently, a cumulative amount @6 ng of human embryonic stem cell (hESC)-derived Lefty or recombinant Lefty (rLefty) or placebo was delivered intratumorally over a 2 week period. (A-C) Tumor cell apoptosis was determined by immunohistochemical staining for terminal deoxynucleotidyl transferase biotin-dUTP nick-end labeling (TUNEL). (D-F) Immunohistochemistry of the Ki67 proliferation marker appears as a brown staining product. (G-T) Periodic acid schiff (PAS) staining of extracellular matrix-rich networks appears as dark grey/black.

Referring to FIG. 18, apoptosis was seen in C8161 melanoma tumor cells injected with Lefty derived from hESCs (H9) and conditioned matrix (A). No apoptosis was evident in the control tumor receiving a sham injection regime of Hank's Balanced Salt Solution (HBSS) (B) or rLefty (C). The proliferation marker Ki67 was not seen in the C8161 melanoma tumors treated with hESC-derived Lefty (D). Ki67 was abundant in the control tumor receiving a sham injection regime of HBSS (E) or rLefty (F). Vasculogenic mimicry was completely abrogated in the C8161 tumors injected with the hESC-derived Lefty (G). In the control tumor receiving no Lefty (H) or rLefty (I) vasculogenic mimicry is obvious. All control tumors received Hank's Basic Salt Solution (HBSS) placebo injections at the same time points as the experimental.

Example 11

Figure 13:
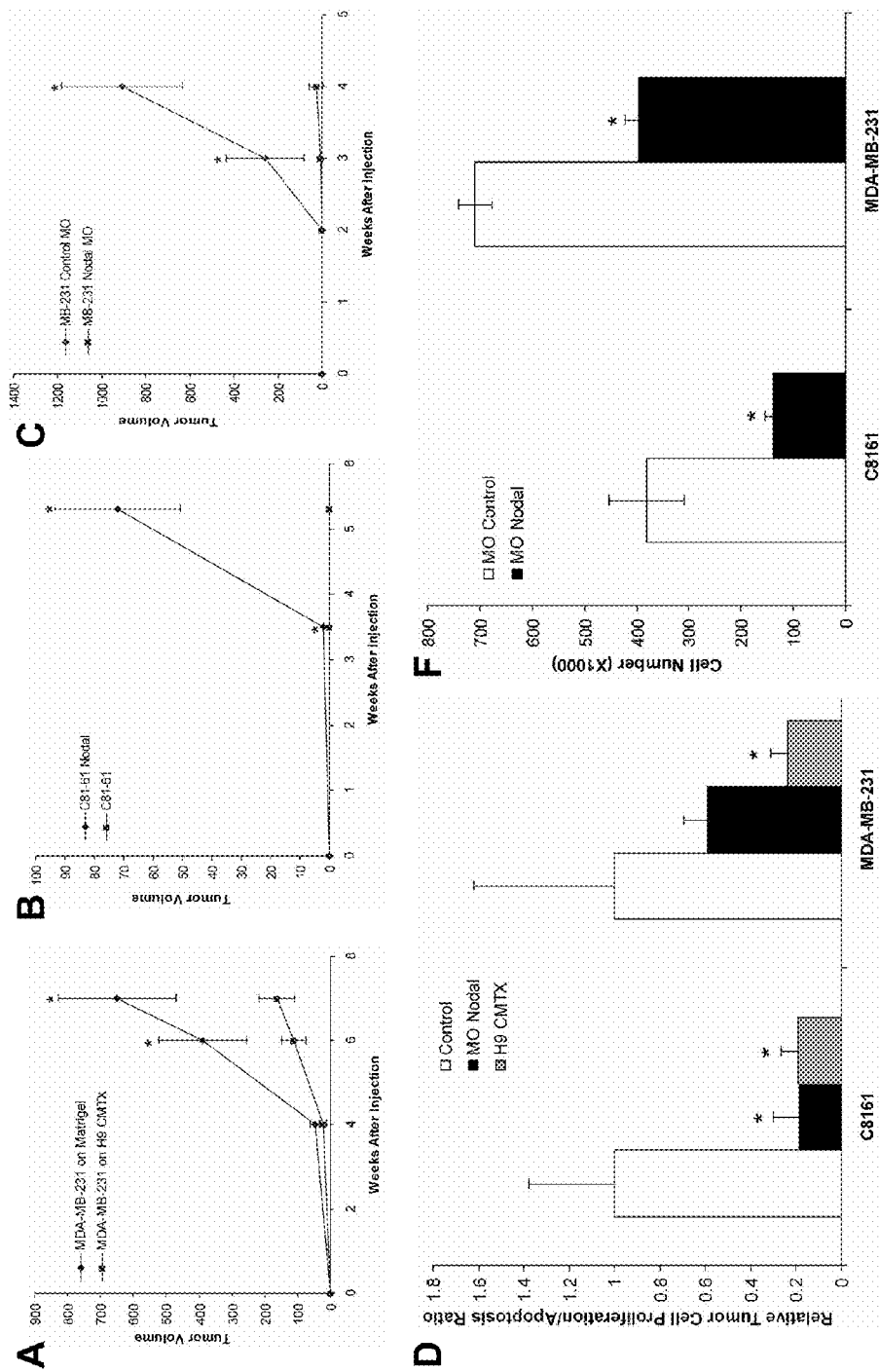
FIG. 13 shows that Nodal inhibition and the microenvironment of hESCs abrogate tumorigenicity in vivo. (A) In vivo tumor formation in a mouse injected with MDA-MB-231 cells pre-exposed for 3 days to either a control matrix (Matrigel) or a matrix conditioned by hESCs (H9 CMTX) (n=10) (B) C81-61 cells, transfected with either an empty vector or a Nodal expression construct (n=5), and (C) MDA-MB-231 cells treated with either $MO^{Control}$ or $MO^{Nodal}$ (n=10). Values represent the mean tumor volume ($mm^3$)±standard error (A) or standard deviation (B,C), and tumor volumes were significantly different at the time points indicated by an asterisk (*) (P<0.05). (D) The ratio of tumor cell proliferation to apoptosis for C8161 and MDA-MB-231 derived tumors, determined by immunohistochemical staining for Ki67 and terminal deoxynucleotidyl transferase biotin-dUTP nick-end labeling (TUNEL). Prior to injection into a mouse, C8161 and MDA-MB-231 cells were cultured for 3 days on control or hESC conditioned (H9 CMTX) matrices, or treated with $MO^{Nodal}$ to knock down Nodal expression. Bars represent mean normalized values standard deviation, and values indicated by an asterisk (*) are significantly different from control values (P<0.05). (E) Immunohistochemical analysis of Ki67 expression (red/brown) and TUNEL staining in orthotopic melanoma (C8161) and breast carcinoma (MDA-MB-231) tumors. Prior to injection into a mouse, cells were treated with $MO^{Nodal}$, exposed to H9 hESC CMTX, or left untreated (control). Proliferation is indicated by Ki67 staining and apoptotic nuclei were detected with confocal microscopy as red staining localized to the nuclei of apoptotic C8161 or MDA-MB-231 cells. For the TUNEL analyses, cell nuclei were counterstained blue with DAPI. Bar equals 25 µm. (F) In vitro proliferation of C8161 and MDA-MB-231 cells treated with either $MO^{Contol}$ or $MO^{Nodal}$. Values represent the mean cell count (×1000)±standard deviation 4 days after the plating of 15,000 cells. An asterisk (*) indicates a significant difference between control and $MO^{Nodal}$ treated cells (n=4, P<0.05).
Figure 13E:
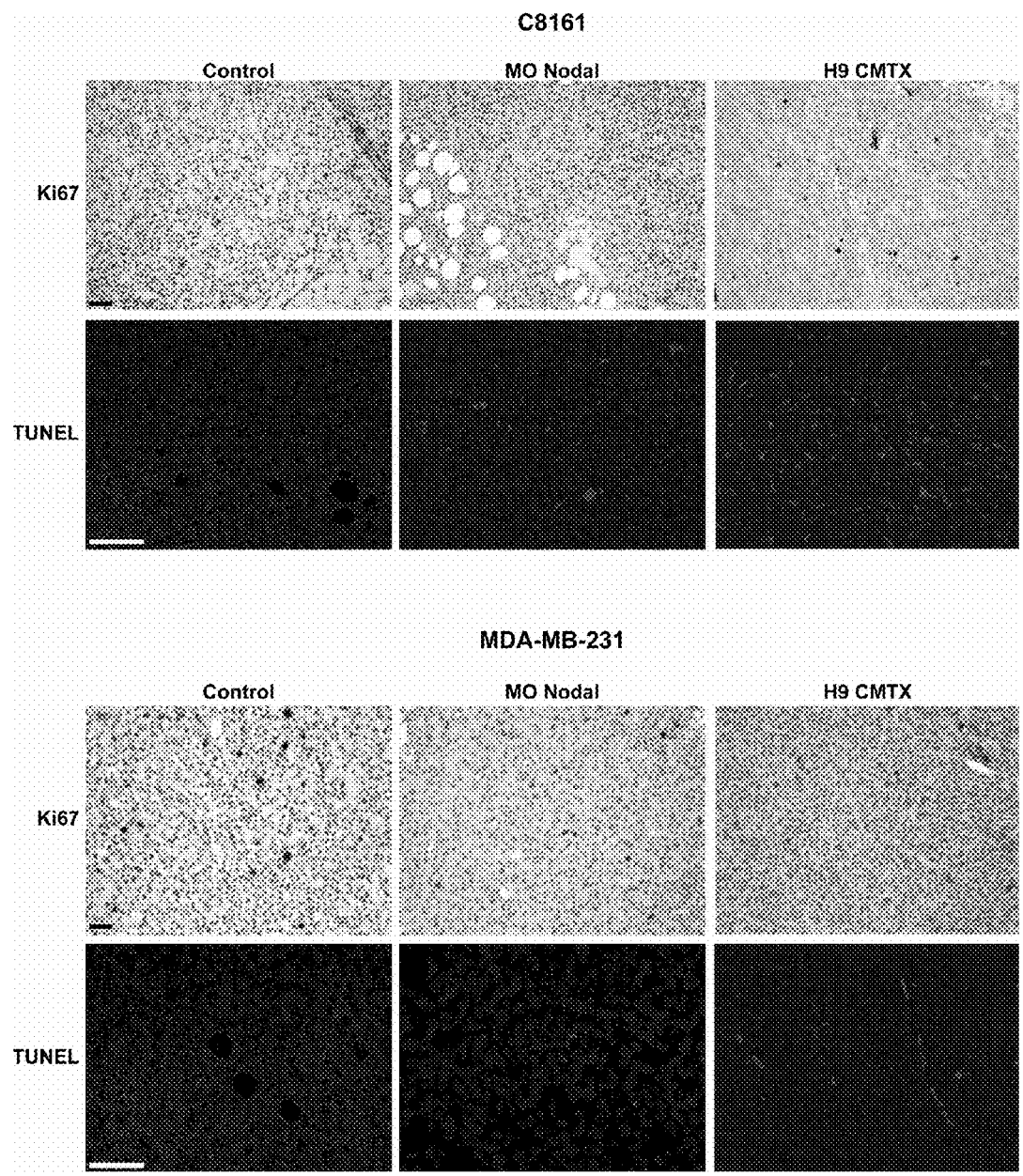

Nodal Inhibition and the Microenvironment of hESCs Abrogate Tumorigenicity In Vivo The effects of the hESC microenvironment on the in vivo tumorigenicity of melanoma and breast carcinoma cells were examined using orthotopic mouse models. Exposure of metastatic melanoma (C8161) and breast carcinoma (MDA-MB-231) cells to H9 CMTX resulted in a significant reduction in tumorigenicity as compared to cells exposed to unconditioned Matrigel (FIGS. 4B & 13A). In order to further substantiate the role of Nodal in tumorigenicity, and to illuminate a potential mechanism for the tumor-suppressive properties of the hESC microenvironment, previously shown to diminish Nodal expression (FIG. 9), orthotopic mouse models were utilized to examine the effects of: (a) Ectopic Nodal expression on the tumorigenic potential of C81-61 cells (isogenetically matched non-tumorigenic variants of the metastatic C8161 melanoma cell line); and (b) Nodal inhibition on MDA-MB-231 breast carcinoma tumorigenicity. The control C81-61 melanoma cell line was unable to form palpable tumors when 500,000 cells were injected, and using gross observation and histology 5.5 weeks after inoculation, these tumor cells could not be detected at the site of injection. In contrast, 100% of C81-61 cells transfected with a Nodal expression vector formed palpable tumors within 3.5 weeks of injection (FIG. 13B). Palpable tumors arose within 2.5 weeks after the injection of 500,000 control MDA-MB-231 cells, and knocking down Nodal expression with Nodal Morpholinos ($MO^{Nodal}$) resulted in a significant reduction in MDA-MB-231 tumorigenicity (FIG. 13C) when the same number of cells were injected.

In order to establish a mechanism by which exposure to the hESC microenvironment abrogates tumorigenicity, the effects of this treatment on the in vivo tumor cell proliferation-to-apoptosis ratio were analyzed. Using immunohistochemical staining for Ki67 as a measure of proliferation, and terminal deoxynucleotidyl transferase biotin-dUTP nick-end labeling (TUNEL) as a measure of apoptosis, it was determined that Nodal knock down and exposure to hESC CMTX correspondingly decreased the ratio of proliferation to apoptosis in metastatic C8161 melanoma cells and in metastatic MDA-MB-231 breast carcinoma cells (FIGS. 13DE & 13E). Moreover, an in vitro analysis of cell proliferation demonstrated reduced proliferation in C8161 and MDA-MB-231 cells treated with MO$^{Nodal}$ relative to cells treated with MO$^{Control}$ (FIG. 13F).

Example 12

Nodal Signaling Essential for Tumor Formation; Inhibitors of Nodal Signaling Reduce Agressiveness and Tumorigenicty The role of Nodal signaling in tumor formation was analyzed, and it was found that downregulation of Nodal signaling results in acquisition of a melanocyte-like phenotype and loss of the dediffernentiated, plastic phenotype.

Administration of an anti-Nodal Morpholino (MO Nodal) also resulted in down-regulation of Nodal, and an in vivo reduction in tumor formation. An in vitro colony forming assay was used to analyze colony-forming ability of poorly aggressive C81-61 cells, aggressive C8161 cells, C8161 cells treated with MO$^{Nodal}$ and C8161 cells treated with MO$^{Nodal}$ and rescued with recombinant Nodal (100 ng/mL). The assay was conducted using 50,000 cells suspended in 0.35% agarose in RPMI containing 10% serum, which were plated into 6-well dishes on 0.5% agar in the same medium. Colonies grew, and pictures were taken at day 7. After 2 weeks, colonies were stained with Crystal Violet and counted.

Figure 14:
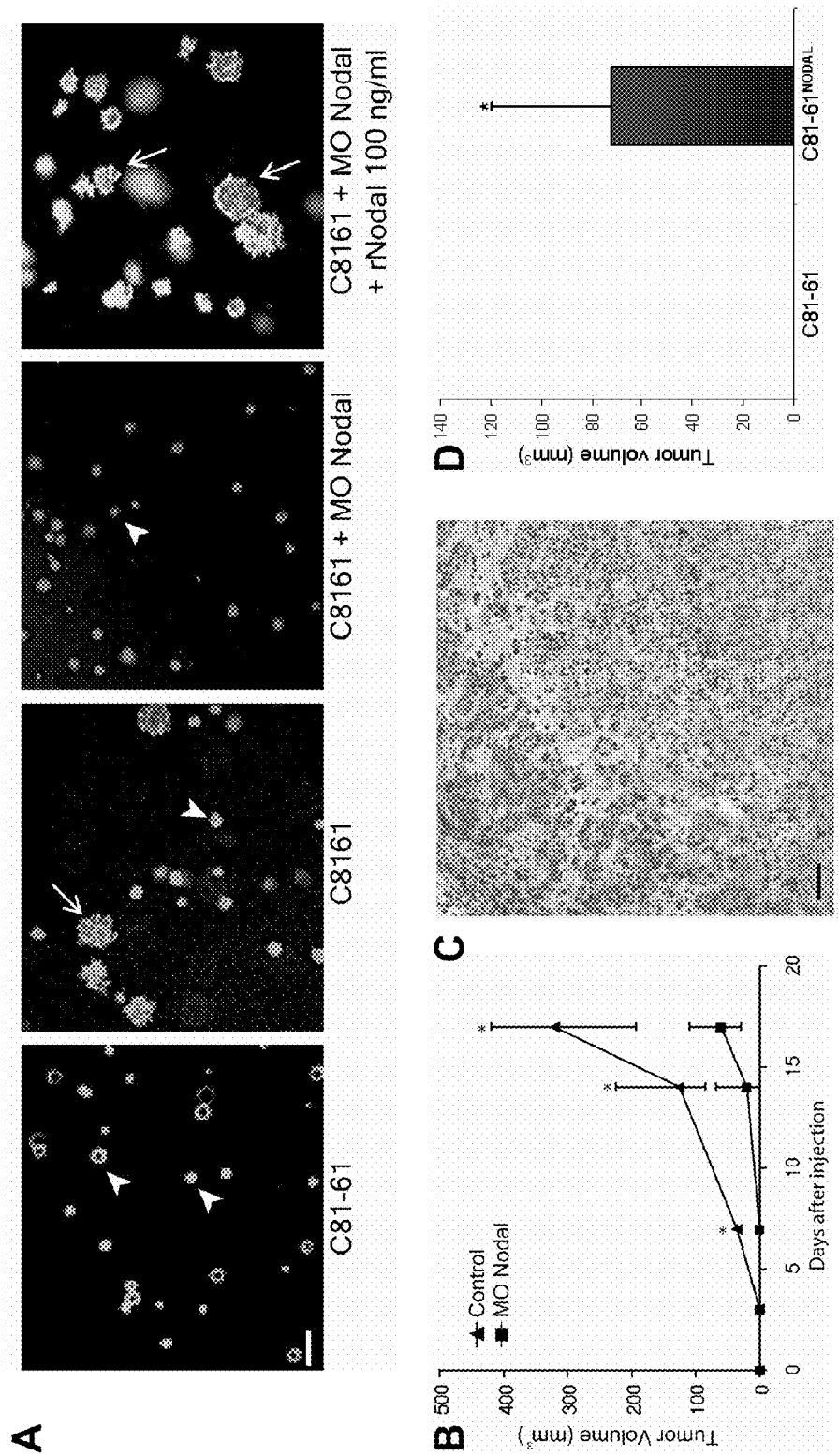
FIG. 14 shows Nodal inhibition abrogates melanoma tumorigenicity. (A) Phase contrast microscopy of cells cultured for 7 days in a soft agar assay. The panels represent the colony-forming ability of poorly aggressive C81-61 cells, aggressive C8161 cells, C8161 cells treated with $MO_{Nodal}$ and C8161 cells treated with $MO_{Nodal}$ and rescued with recombinant Nodal (100 ng/mL). Bar equals 20 µm. (B) In vivo tumor formation in a mouse injected with C8161 cells treated with either $MO_{Control}$ or $MO_{Nodal}$. Values represent the median tumor volume ($mm_3$)±interquartile range, and the $MO_{control}$ and $MO_{Nodal}$ tumor volumes were significantly different at the time points indicated by an asterisk (*) (n=5, p<0.05). (C) Immunohistochemical analysis of Nodal staining in an orthotopic tumor derived from C8161 cells treated with $MO_{Nodal}$. The C8161 cells have begun to re-express Nodal by 17 days post-injection. Bar equals 50 µm. ($MO_{Nodal}$=antisense morpholino to Nodal). (D) Acquisition of tumorigenic potential by C81-61 poorly aggressive melanoma cells transfected with Nodal cDNA, compared with mock transfected C81-61 control: Values are reported as median tumor volume after 38 days±standard deviation (*p<0.05; n=5/parameter).

Utilizing the in vitro assay, it was found that C8161 cells were able to form colonies in soft agar within 7 days, and that their less aggressive isogenic counterparts (C81-61) were not clonogenic (FIG. 14A). Nodal inhibition with MO$_{Nodal}$ significantly diminished the ability of C8161 cells to undergo anchorage-independent growth. Even after 2 weeks, MO$_{Nodal}$ reduced the colony formation of the C8161 cells by 57% (n=16, p<0.001), a phenomenon that was rescued by the inclusion of rNodal (100 ng/mL). Interestingly, rNodal did not induce colony formation in the C81-61 cell line. For the clonogenic assays, statistical significance was determined using a test. In all cases, differences were statistically significant at p<0.05.

As a corollary to these findings, an orthotopic mouse model was used to examine the effect of Nodal inhibition on melanoma tumor formation. For the experimental tumourigenesis model, 5 week old nude mice (Harlan, Madison, Wis.) were injected subcutaneously with 250,000 C8161 cells, treated with control or anti-Nodal Morpholinos, in 50 µL of complete RPMI. Tumor measurements were taken on days 3, 7, 14 and 17 post-injection, and mice were sacrificed on day 17. In vivo tumor formation in a mouse injected with C8161 cells treated with either MO$_{Control}$ or MO$_{Nodal}$ is shown in FIG. 14B. For the orthotopic mouse tumor formation studies, statistical significance was determined using the Kruskal-Wallis One Way Analysis of Variance on Ranks, followed by Dunn's method.

Palpable subcutaneous tumors arose within 7 days following the injection of only 250,000 control C8161 cells. In contrast, knocking down Nodal expression resulted in a significant reduction in C8161 tumorigenicity (FIG. 12B; n=5, p<0.05) when the same number of cells were injected. This reduction in tumorgenicity was characterized by 30% diminution of tumor incidence as well as a decrease in tumor growth.

Immunohistochemistry was used to analyze tumors from the mice, which showed that the tumors that formed in the MO$_{Nodal}$ treatment group started to regain Nodal expression by day 17 (FIG. 14C).

Additionally, poorly aggressive melanoma cells (C81-61) cells acquired tumorigenic potential when transfected with Nodal cDNA. C81-61 cells were transfected with either an empty vector or a Nodal expression construct (n=5). As shown in FIG. 14D, such cells demonstrated tumor growth.

Figure 15:
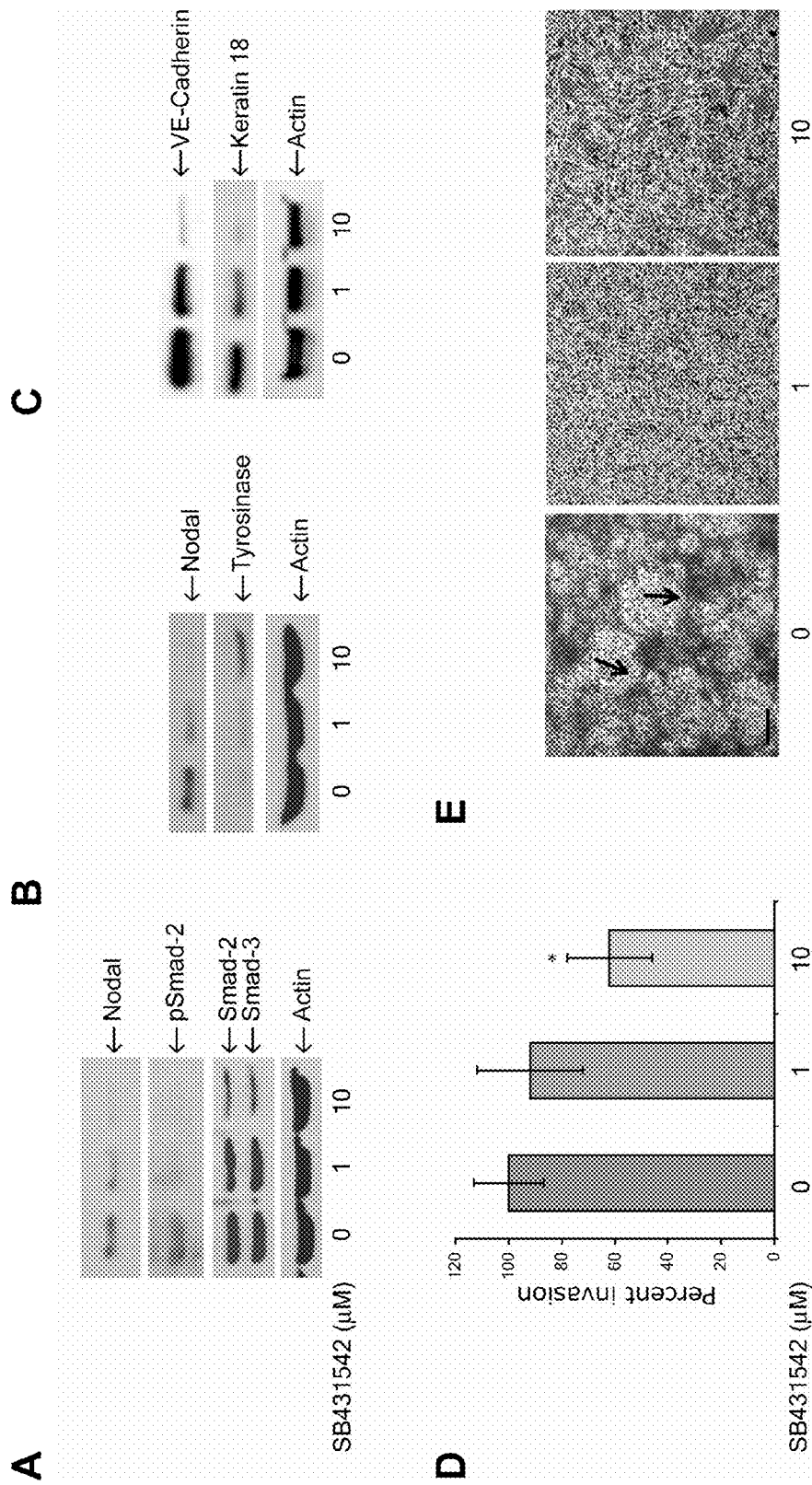
FIG. 15 shows down-regulation of Nodal signaling results in acquisition of a melanocyte-like phenotype and loss of the dedifferentiated, plastic phenotype. (A) Western blot analyses of Nodal, phosphorylated SMAD-2, total SMAD 2/3, and Actin in C8161 cells 48 hours after administration of either vehicle or an ALK 4/5/7 inhibitor (SB431542, 1 µM, 10 µM). (A,B) All Nodal bands represent the pro-protein. (B) Western blot analyses of Nodal, Tyrosinase and Actin in C8161 cells 24 hours after the administration of either vehicle or different concentrations of ALK inhibitor while (C) is a Western analyses for VE-Cadherin, Keratin 18 and Actin in C8161 cells cultured on 3-D collagen I matrices for 6 days in the presence of vehicle or different concentrations of ALK inhibitor. (D) Reduction in invasive ability and (E) abrogation of vasculogenic mimicry following down-regulation of Nodal with ALK 4/5/7 inhibitor.

Administration of an ALK 4/5/7 inhibitor resulted in a reduction of the expression of various vasculogenic mimicry plasticity biomarkers. FIG. 15A shows Western blot analyses of Nodal, phosphorylated SMAD-2, total SMAD 2/3, and Actin in C8161 cells 48 hours after administration of either vehicle or an ALK 4/5/7 inhibitor (SB431542, 1 µM, 10 µM). All Nodal bands represent the pro-protein. FIG. 15B shows Western blot analyses of Nodal, Tyrosinase and Actin in C8161 cells 24 hours after the administration of either vehicle or different concentrations of ALK inhibitor while FIG. 15C shows a Western analyses for VE-Cadherin, Keratin 18 and Actin in C8161 cells cultured on 3-D collagen I matrices for 6 days in the presence of vehicle or different concentrations of ALK inhibitor. FIG. 15D shows a reduction in invasive ability and FIG. 15E shows an abrogation of vasculogenic mimicry following down-regulation of Nodal with ALK 4/5/7 inhibitor.

The experiments described above revealed that metastatic melanomas express the embryonic morphogen Nodal, that Nodal is essential for tumor formation, and that its effects can be mitigated through Nodal pathway inhibition, either directly or indirectly (e.g. through ALK inhibition).

Example 13

Nodal Expresssion is Down-Regulated by Notch Inhibition

To address the possible molecular mechanisms underlying the reprogramming of melanoma cells exposed to the hESC matrix microenvironments, an analysis of the Nodal promoter was initiated, a putative binding sequence effector for the Notch pathway (CBF-1) was discovered, and the possibility of molecular cross-talk between the Notch and Nodal pathways was investigated. Nodal expression in metastatic melanoma cells treated with Notch siRNAs was knocked down, particularly with Notch 4 siRNA. Conversely, Notch expression was relatively unaffected by knockdown of Nodal, suggesting that Notch is upstream of Nodal with possible molecular cross-talk.

Figure 16:
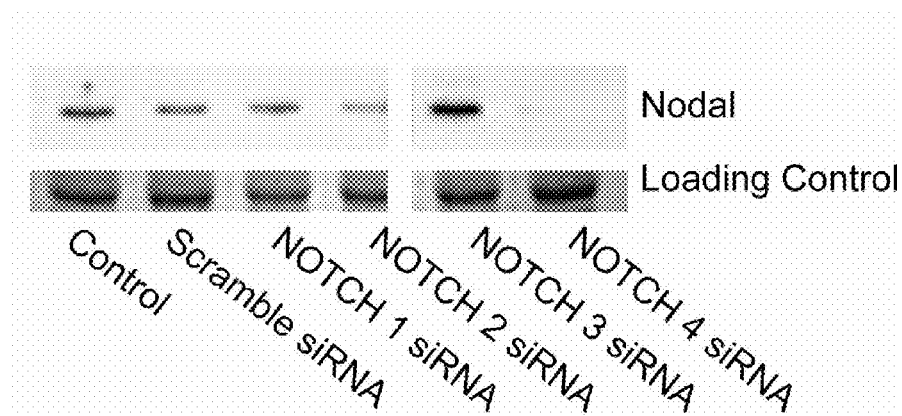
FIG. 16 shows molecular cross-talk between Nodal and Notch. (A) Knockdown of Nodal expression in C8161 cells by Notch siRNAs, particularly Notch 4 siRNA. Western blot analysis of C8161 cells 72 hrs following the administration of siRNA. Real-time RT-PCR and Western blot analyses confirmed the silencing of each Notch at this time points. (B) Notch expression is relatively unaffected by knockdown of Nodal in C8161 cells. Western blot analysis of Notch 1, 2 and 4 in C8161 cells treated with the Nodal inhibitor SB431542.
Figure 16:
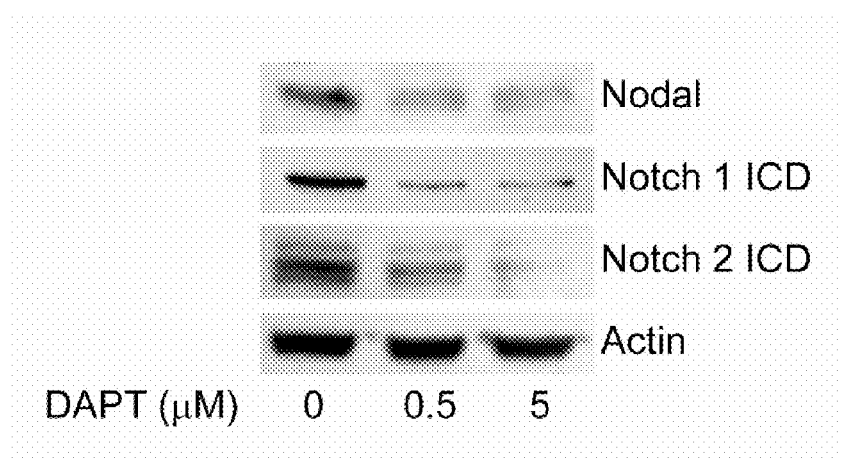

As shown in FIG. 16A, Nodal expression was knocked down in C8161 cells 72 hrs following the administration of Notch siRNA. Real-time RT-PCR and Western blot analyses confirmed the silencing of each Notch at this time point. In contrast, as shown in FIG. 16B, Notch expression is relatively unaffected by the knockdown of Nodal (via treatment with the Nodal inhibitor SB431542) in C8161 cells.

Example 14

Hypermethylation Plays a Role in the Nodal Pathway in Aggressive Tumor Cells

Hypermethylation of Nodal was observed in the highly metastatic C8161 cells, but not in the isogenically matched C81-61 melanoma cells, nor in melanocytes or hESCs (H9). Sequencing based methylation analyses, therefore, could be used to indicate the methylation status in human tumors, and hence serve as a valuable prognostic marker for disease state.

Nodal's methylation status is supported by work in Feinberg's laboratory showing that CTCF binding site methylation separates enhancers from promoters. (Gius, et. al., 2004, Cancer Cell 6:361-371) In that work, it was found that azacytidine shut down expression of as many genes as it activated; it is known now that this subset of genes contains CTCF binding sites within the promoter CpG island. In particular for Nodal, the sequence is CCGCGCTGGGTGC-CCAG [SEQ ID NO: 1]. The consensus that was identified in genes activated by methylation is CCGCGN(N)GG(G)(N) GCC(N)CAG [SEQ ID NO:2], and Feinberg has directly demonstrated methylation dependent activation, with CTCF insulator binding abrogation in several promoters with this consensus sequence. Paradoxically, when this site is methylated, CTCF can no longer bind, and the promoter is enabled. This is a major imprinting mechanism, and has significant implications for how Nodal may be regulated during both cancer and development.

Figure 17:
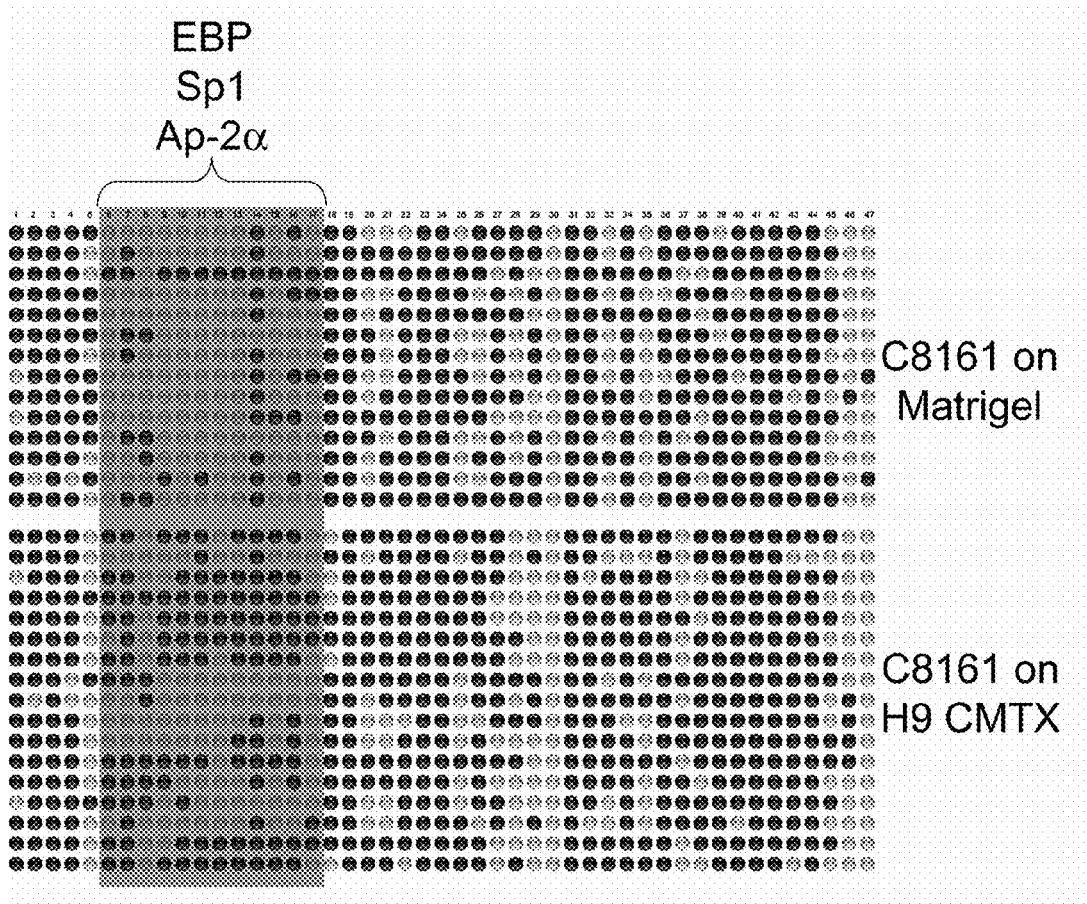
FIG. 17 shows that exposure of aggressive C8161 human melanoma cells to matrices conditioned by hESCs induces an increase in the methylation of specific cytosine residues (CpG residues 6-17) in the first half of the CpG island in the Nodal promoter. The graphs depict the methylation status of the first half of the Nodal CpG island in aggressive C8161 human cutaneous melanoma cells cultured on either Matrigel or on Matrigel conditioned by H9 hESCs. Each circle represents a CpG dinucleotide in the CpG island. Black and grey circles symbolize methylated and unmethylated residues respectively. Each row represents an individual clone or allele. Although culture in the presence of a hESC microenvironment (H9 CMTX) globally increases methylation by only 6.8%, the shaded area experienced a 32% increase in methylation when cells were cultured on H9 CMTX versus Matrigel alone.

Referring to FIG. 17, although culture of the C8161 cells in the presence of a hESC microenvironment (H9 CMTX) globally increases methylation by only 6.8%, the shaded region has a 32% increase in methylation when cells are cultured on H9 CMTX versus Matrigel alone. Sequence alignment revealed that the differentially methylated cytosines are associated with putative transcription factor binding sites. The shaded area contains consensus sequences for EBP, Sp1 and AP-2alpha, and the 32% increase in methylation in this region may indicate a silencing of the Nodal gene in the tumor cells exposed to the hESC CMTX.

Example 15

Exemplary Assays and Procedures

General Maintenance of Cell Lines
The derivation and phenotypic characteristics of the human melanoma cell lines have been previously described. Seftor, et. al., 2002, *Clin. Experim. Metastas.* 19:233-246; Seftor, et. al., 2005 *Cancer Res.* 65:10164-10169. The melanoma cell lines are maintained in RPMI 1640 medium (Invitrogen) supplemented with 10% fetal bovine serum (FBS, Gemini Bioproducts) and 0.1% gentamycin sulfate with the exception of C81-61 cells which are maintained in Ham's FIO medium supplemented with 15% FBS, 1X Mito+ (BD Bioscience) and gentamycin sulfate. Normal human melanocytes are purchased (Cascade Biologics) or isolated from neonatal foreskins. Seftor, et. al., 2005. A single cell suspension is prepared, added to plastic flasks for the adherence of melanocytes and the cells propagated in Medium 254 with Human Melanocyte Growth Supplement (Cascade Biologics) including, 100 units/ml penicillin, 100 µg/ml streptomycin, and 250 ng/mL amphotericin B. The human embryonic stem cell lines are cultured as previously described. Thomson, et. al., 1998, *Science* 282:1145-1147. Briefly, cells are grown in 6-well plates precoated with 0.1% porcine gelatin and containing $1.9 \times 10^5$ irradiated mouse embryonic fibroblasts (strain CF-1; ATCC) per well. The cells are maintained in medium containing DMEM/F12 (1:1), 20% knock-out serum replacement, non-essential minimal amino acids, L-glutamine (Invitrogen), β-mercaptomethanol, and 4 ng/ml FGF-2 (R&D Systems), and are split with collagenase (1 mg/ml) before the colonies begin to overlap. The cultures are determined to be free of mycoplasma contamination using a PCR-based assay (Roche). The normal human neonatal epidermal melanocytes (HEMn-LP; Cascade Biologics, Portland Oreg.), myoepithelial cells (Hs 578 Bst; American Type Culture Collection (ATCC), Manassas, Va.) and primary mammary epithelial cells (HMEpC; Cell Applications Inc., San Diego Calif.) were maintained as per distributor instructions. Live umbilical cord blood stem cells (SC00125; New Jersey Stem Cell Resource at Coriell Institute for Medical Research) amniotic fluid derived stem cells (GM00473, GM00957A) and adult bone marrow derived mesenchymal stem cells (Stem Cell Technologies, Vancouver BC, Canada) were maintained under the recommended conditions. The HTR-8/SVneo is a well characterized immortalized human extravillous cytotrophoblast cell line, and was maintained as previously described Graham et al., 1993, *Exp. Cell Res.* 206:204-211. Recombinant Nodal and Lefty (R&D Systems) were diluted as per manufacturer suggestions. The expression vector for wild type Nodal was kindly provided by Dr. Daniel Constam (Swiss Institute for Experimental Cancer Research (ISREC), Epalinges, Switzerland) and was transfected into C81-61 cells as previously described. Le Good et al., 2005, *Curr. Biol.* 15:31-36.

Preparation/Preconditioning of 3-D Human Matrices
25-30 µl of a defined human matrix (50 µg/ml human laminin; 50 µg/ml human collagen IV in a 3 mg/ml human collagen I base; Sigma) are either spread onto coverslips or directly placed into 12-well culture dishes and polymerized with an application of 100% ethanol at room temperature. After extensive washes with PBS, hESC's are seeded onto the 3-D matrix in complete stem cell medium. After 3-4 days images are captured digitally using a Zeiss Televal inverted microscope and Hitachi HV-C20 CCD camera. The cells are then removed with 20 mM $NH_4OH$ followed by thorough washes with sterile water, PBS and then complete medium. The conditioned matrix is then analyzed by 2-D LDS-PAGE and Western blot directly, or reseeded with melanoma cells and incubated for an additional 3 days. The cells re then harvested for further biochemical, molecular and functional analyses.

3-D Conditioned Matrix Experiments
Conditioned matrices were prepared using hESCs, melanocytes, myoepithelial cells, amniotic fluid derived stem cells, or trophoblast cells on growth factor-reduced Matrigel (14 mg/mL; BD Biosciences) as previously described. Postovit al., 2006, Stem Cells 24: 501-505. In all cases, cells were 80-100% confluent during the conditioning of the matrix. Alternatively, hESC-derived Lefty protein was seeded into Matrigel prior to polymerization. Human melanoma (C8161) or breast carcinoma (MDA-MB-231) cells, $2.5 \times 10^5$ cells/6-well dish, were subsequently exposed to this preconditioned matrix for 3 to 4 days.

Invasion/Migration Assay
The Membrane Invasion Culture System (MICS) chamber is used to evaluate the degree of tumor cell invasion through matrices in vitro (both stimulated and unstimulated) as described previously. Hendrix, M. J. C. et. al., 1992, *J. Natl. Cancer Inst.*, 84:165-174.

Determination of Cell Viability and Proliferation
Cell proliferation is assayed by immunohistochemical staining of BrdU incorporation into newly synthesized DNA of replicating cells at various time points (BrdU Labeling and Detection Kit III; Roche). Assessment of proliferation index is monitored by Ki-67 expression.

Proliferation Assay
$1.5 \times 10^4$ cells were plated in individual wells of a 24-well dish under standard tissue culture conditions and cell counts were taken daily following harvesting.

Soft Agar Clonogenic Assay
Clonogenicity of cells are assessed as previously described. Hamburger, A. W., and Salmon, S. E., 1977, *Science* 197:461-463. Each parameter is tested in triplicate for clone formation in soft agar. Briefly, 104 cells are plated in 60 mm Petri dishes in complete medium placed over the soft agar. On specific days after the cells are plated, phase contrast images of the colonies are taken using a Zeiss Axiovert 25 with an Hitachi HCV-20 color camera.

Anchorage Independent Growth Assays

Anchorage independent growth assays were conducted as previously described. Topczewska et al., 2006, *Nat. Med.* 12: 925-932.

Differentiation Assays of Stem Cell Populations and Clonally-Derived Melanoma Stem Cells Stem cells from the various 3-D preconditioned matrices are harvested and replated on an appropriate ECM in a specified differentiation media, as previously described. Hendrix et. al., 2003, *Nature Rev. Cancer* 3:411-421; Hsu et. al., 2004, *Methods Mol. Med.* 107:13-28; Pittenger et. al., 1999, *Science* 284:143-147

Experimental Orthotopic Tumor Models 5 week old mice were injected subcutaneously with 250,000 C8161 or 500,000 C81-61 human cutaneous melanoma cells in 50 μL of complete RPMI; or 500,000 MDA-MB-231 cells in 50 μL of complete RPMI were injected into the mammary fat pad of 8 week old mice. When tumors became palpable measurements were taken twice per week.

2-D L(ithium)DS-PAGE and Western Blot

Analysis of extracellular matrix components before and after conditioning by the different cells is performed using Invitrogen's 3-10 pH IPG strips in the first dimension and 4-12% Bis/Tris LDS-polyacrylamide gradient gels in the second dimension using MES (proteins up to ~100 kDa) or MOPS (proteins>100 kDa) reservoir buffers, as per the manufacturer's protocols. The gels are stained with Sypro Red then electroblotted onto Immobilon P membranes (Millipore) for Western analysis using specific extracellular matrix antibodies (Chemicon; R&D Systems; Life Technologies).

Recovery of Lefty from Cell Conditioned Matrices

M-280 tosylactivated Dynabeads (Dynal Biotech) are covalently coupled to anti-Lefty antibody (M-20:sc7408; Santa Cruz Biotechnology, Inc.) at a final concentration of 8 μg antibody/1×10$^7$ beads as per the manufacturer's protocol. The cell conditioned matrix is solubilized in RIPA buffer, sonicated, centrifuged and the supernatant mixed by rotation with the beads for 1 hour at 4° C. After washing twice with PBS, Lefty is recovered using either 50 mM glycine-HCl (pH 3.0), then normalized to pH 7.4 with a 0.1 volume of 1 M Tris pH 8.5, or 0.2 M Tris pH8.5 plus 0.5 M NaCl.

RNA Extraction and Reverse Transcriptase Polymerase Chain Reaction (RT-PCR)

Total RNA was isolated using TRIzol reagent (Invitrogen) and 1 μg was reverse transcribed as previously described. Topczewska et al., 2006. Real-time PCR was performed as previously described (Id.) using TaqMan® gene expression human primer/probe sets for the following genes:VEGF (Hs00173626_m1), TSP-1 (Hs00170236_m1), Ki67 (Hs00606991_m1), Lefty1/B (Hs00764128_s1), Nodal (Hs00250630_s1). Target gene expression was normalized to the endogenous control gene GAPDH (GAPDH: 4333764F), RPLPO (RPLPO: 4333761F) and/or 18S rRNA (Hs99999901_s1). Data was analyzed using Applied Biosystems Sequence Detection Software (Version 1.2.3).

FACs Analysis/Sorting

Fluorescence Activated Cell (FAC) analyses and sorting are conducted using the BD FACsAria. Prior to FAC analysis, cells are incubated with antibodies as per manufacturer instructions and intracellular proteins detected in cells that have been previously permeabilized. The FAC protocols are optimized for both cell surface proteins (such as CD34) and intracellular proteins (such as keratins). Live cell sorts are conducted using a 100 μm nozzle and aseptic technique. Successful live sorts are performed against cell surface proteins, fluorescently labeled cells and cells containing fluorescent anti-sense Morpholinos.

Glycoprotein Determination

Protein lysates underwent SDS-polyacrylamide gel electrophoresis and transfer and were stained for glycoproteins using the Pro-Q Emerald 300 staining kit (Molecular Probes). After drying the blot, glycoproteins were visualized using an ultraviolet tansilluminator and an image of the green fluorescing proteins captured using a color CCD camera (Toshiba) equipped with a deep yellow #15 filter. The blot was then rehydrated as per the manufacturer's instructions and Lefty protein was detected with immunoblotting.

IVIS Imaging System 200 Series

Real-time biophotonic imaging of GFP-labeled tumor cells in the mouse model(s) is performed using a Xenogen IVIS Imaging System 200 Series imager. This system contains a custom lens and improved resolution with single cell sensitivity for in vitro analyses. A laser scanner and associated software provides an ability to perform 3-D surface topography for single-view diffuse tomographic reconstructions of internal sources in order to track tumor formation and metastatic potential of GFP-labeled tumor cells. Quantitative in vivo assays are performed using dual reporters to differentiate increases in cell proliferation from increases in specific gene expression.

Laser Capture Microdissection

The Veritas Laser Capture Microdissection (LCM) system (Arcturus) combines a three objective lens microscope (up to 40×) for visualizing a sample mounted on a slide and selecting the areas of interest, a UV laser for cutting around the perimeter of the areas of interest, and a IR laser that melts and thereby sticks the surface of a collector cap to these areas, or individual cells for isolation. The Veritas LCM can be used for isolating live cells cultured on 3-D matrices which have been cast in the etched space of a specially made membrane containing slide compatible with the Veritas system (PEN frame slides). Captured material is subsequently lysed for RNA isolation (Picopure, Arcturus) and downstream applications including Q-PCR and microarray gene expression analysis.

Confocal Immuno-Microscopy

Immuno-confocal microcopy is performed using a Zeiss LSM 510 META Confocal Microscope. Prior to analysis, 3-D cultures or tissue sections are incubated with specific antibodies against target proteins as per protocols previously established in the laboratory.

In Situ Hybridization

3-D cultures or tissue samples are placed on subbed microscope slides, and prepared as previously described. Kulesa, et. al., 2000, *Develop.* 127(13):2843-2852.

Nodal and Lefty Knockdown

Nodal, and Lefty protein expression were inhibited using anti-sense Morpholino oligonucleotides (Gene Tools Inc., Philomath, Oreg.). The Morpholino sequences were selected based on manufacturer's recommendations (21-25 mer anti-sense). Fluoroscein (FITC)-conjugated control (5'-CCTCT-TACCTCAGTTACAATTTATA-3') [SEQ ID NO: 19], Nodal (5'-AAGCAGCACCTCCAGCCCTTATATC-3') [SEQ ID NO: 20], Lefty-A (5'-GCCACATGGTGCTGCCCTGGG-3') [SEQ ID NO: 21], and Lefty-B (5'CTGCATGGTGCTGC-CCTGGAGGA-3') [SEQ ID NO: 22]. Morpholinos (20 μM) were delivered using the scrape method. Topczewska et al., 2006. Cancer cells were sorted for FITC and were recovered for 1 day prior to experimentation.

Knockdown of Gene Expression by siRNA

Cells are plated in 6-well tissue culture plates and allowed to grow to 50% confluence in serum containing, antibiotic-free medium. The cells are then transfected with 10 or 100 nM of a gene-specific siRNA or a non-specific siRNA control using oligoFECTAMINE according to manufacturer's specifications (Invitrogen). The cells are then harvested 3 days post transfection and assessed for gene expression by RT-PCR, Q-PCR and Western blot analysis, as well as functional assays. Quantitative PCR (Q-PCR): Total RNA is isolated from cells using Trizol RNA isolation reagent (Invitrogen) according to manufacturer's specifications. Reverse transcription of the total RNA is performed in a Robocycler gradient 96 thermocycler (Stratagene) using the Advantage PCR kit according to the manufacturer's instructions (Clontech). Q-PCR is performed using a 7500 Real Time PCR System (Applied Biosystems) and TaqMan® gene expression primer/probe sets (Applied Biosystems). Briefly, 5 µl cDNA, 1.25 µl 20× Assays-on-Demand Gene Expression Assay Mix and 12.5 µl 2× TaqMan® Universal PCR Master Mix in a total of 25 µl are amplified with the following thermocycler protocol: 1 cycle at 50° C. for 2 min; 1 cycle at 95° C. for 10 min; and 40 cycles at 95° C. for 15 seconds/60° C. for 1 min. All data is analyzed with the Sequence Detection Software (version 1.2.3, Applied Biosystems), and expression of each target gene normalized to an endogenous control gene. Each experiment is repeated twice and each sample is performed in triplicate.

Microarray Analysis

Microarray and bioinformatics analyses of the cells is performed using the U133A Human Genome Array from Affymetrix as a cooperative agreement with Translational Genomics (TGen; Phoenix, Ariz.; Dr. Jeffrey Trent).

Comparative Genomic Hybridization Analysis: Genomic DNA Isolation

Genomic DNA is isolated from cells using the PUREGENE DNA isolation kit (Gentra Systems). Five µg of gDNA is digested with EcoRI, extracted with phenol:chloroform, ethanol precipitated, and resuspended in sterile distilled water, as previously described. O'Hagan et. al., 2003, *Cancer Res.* 53:5352-5356.

Statistical Analysis

All statistical analyses are performed using Microsoft Excel's spreadsheet software with the majority of statistics consisting of a "one-way analysis of variance" (ANOVA) determination with a value of $p \leq 0.05$ deemed significant. For the orthotopic mouse tumor formation studies, we determined statistical significance using the Kiruskal-Wallis One Way Analysis of Variance on Ranks, followed by Dunn's method or a one way analysis of variance (ANOVA) followed by the Student-Newman-Keuls method for pairwise multiple comparisons. For the clonogenic and proliferation assays we determined statistical significance using ANOVA followed by the Student-Newman-Keuls method for pairwise multiple comparisons. For the correlation of breast cancer stage and Nodal expression, a Spearman Rank Order Correlation was employed. In all cases, differences were statistically significant at $P<0.05$.

Analysis of DNA methylation by sequencing of sodium bisulfite-treated DNA

Genomic DNA is obtained by digestion with proteinase K (Quiagen) followed by phenol/chloroform extraction, and is subjected to sodium bisulfite treatment to modify unmethylated cytosine to uracil using the 'CpGenome™ DNA Modification Kit'(Chemicon International). Bisulfite-treated DNA is amplified by a nested-PCR protocol using the primers described in Table 1.

TABLE 1

Primers used for amplifications after DNA bisulfite conversion.

| Primer | Sequence | |
|---|---|---|
| *NODAL gene CpG1 (52 CpGs)* | | |
| NODAL-1 EF | 5' - TTT TAG AAG GGA GTG AAT TGG - 3' | (SEQ ID NO: 3) |
| NODAL-1 ER | 5' - AAA AAA TAA AAA CTT CTA ATC TCC - 3' | (SEQ ID NO: 4) |
| NODAL-1 IF | 5' - AGT ATT TTA GTA AAT TTT TTA TTG - 3' | (SEQ ID NO: 5) |
| NODAL-1 IR | 5' - ATT AAT ATT ACT ATA ATA ATT TAA TC - 3' | (SEQ ID NO: 6) |
| *NODAL gene CpG2 (47 CpGs)* | | |
| NODAL-2 EF | 5' - TAA TTT TAT AAG ATT GGA GAT TAG - 3' | (SEQ ID NO: 7) |
| NODAL-2 ER | 5' - TAC TAA AAC CCA AAA TAT AAA AAC - 3' | (SEQ ID NO: 8) |
| NODAL-2 IF | 5' - TTT AAA TTA AAA TTT AGA GAT AAT GG - 3' | (SEQ ID NO: 9) |
| NODAL-2 IR | 5' - ACT TTC AAA CCT AAC CAA CCC - 3' | (SEQ ID NO: 10) |
| *LEFTY 1 (B) (61 CpGs)* | | |
| LEFTY1 EF | 5' - TAG TTT TTA AGG TTT AGG GTG TG - 3' | (SEQ ID NO: 11) |
| LEFTY1 ER | 5' - TAC TAA CCC TAC TCT TAT CCC - 3' | (SEQ ID NO: 12) |
| LEFTY1 IF | 5' - AG TTT TAG TTG GGG TTT TTT AAG - 3' | (SEQ ID NO: 13) |
| LEFTY1 IR | 5' - TTA AAA ACC AAC ACA CAC CTA C - 3' | (SEQ ID NO: 14) |
| *LEFTY 2 (A) (66 CpGs)* | | |
| LEFTY2 EF | 5' - TAG TTT TTG AGG TTT AGG GTG TG - 3' | (SEQ ID NO: 15) |
| LEFTY2 ER | 5' - TAT CTC CTA ACC TAA CTA CC - 3' | (SEQ ID NO: 16) |
| LEFTY2 IF | 5' - AG TTT TAG TTG GGG TTT TTT AAG - 3' | (SEQ ID NO: 17) |
| LEFTY2 IR | 5' - CTC AAT AAC CCT ACC ATC CTC - 3' | (SEQ ID NO: 18) |

*EF/R = external primer set; IF/R = internal primer set

PCR is performed in a volume of 25 µl containing PCR Buffer (Qiagen); 1.5 mM of MgCl2 (Qiagen); 200 µM of dNTPs (Invitrogen); 0.32 µM of each primer and 1 U of Hot Start Taq Plus DNA Polymerase (Qiagen). The PCR conditions are: 94° C. for 10 min, 94° C. for 3 min, 48° C. for 3 min, 72° C. for 2 min one cycle; 94° C. for 3 min, 50° C. for 3 min, 72° C. for 2 min five cycles and 94° C. for 1 min, 52° C. for 1 min, 72° C. for 1 min 35 cycles for the first reaction and the same annealing temperatures (48°, 50° and 52° C.) for the nested reaction. Amplified products are purified using the Gel Purification Kit (Qiagen) and are ligated to a vector using the TOPO TA Cloning Kit (Invitrogen). Twenty four positive clones are sequenced for each sample using the vector's forward and reverse primers. DNA sequencing reactions are performed using the 'DNA dRhodamine Terminator Cycle Sequencing Ready reaction' kit (Applied Biosystems) and an ABI3730x1 sequencer (Applied Biosystems) according to the manufacturer's instructions.

Immunoblotting

Protein lysates were prepared and quantified as previously described in Hess et al., 2001, *Cancer Res.* 61:3250-3255. Equal amounts of protein were separated by SDS-polyacrylamide gel electrophoresis under reducing conditions, and the resolved proteins were transferred onto Immobilon-P membranes (Millipore Corp., Bedford, Mass.). Membranes were blocked in 1% TBS, 0.1% Tween 20 (TBS-T) and 5% dry milk powder or 3% gelatin (for Nodal Westerns). Blots were incubated with primary antibody (Table 2), washed in TBS-T or TBS-T containing 0.5M NaCl for the Nodal Westerns, and incubated with the appropriate horseradish peroxidase-labeled secondary antibody. Secondary antibodies were detected by enhanced chemiluminescence (Super Signal; Pierce, Rockford, Ill.) and exposure to autoradiography film (Molecular Technologies, St Louis, Mo.). Nodal protein was detected as two major bands at ~48 and ~35 kDa representing precursor and pro-Nodal respectively. Nodal often appeared as multiple bands, likely due to degradation of protein modifications.

TABLE 2

Antibodies Utilized for Western Blot (WB), Immunohistochemical (IHC) and Immunofluorescence (IF) Analyses.

| Antibody | Concentration & Use | Company |
| --- | --- | --- |
| Polyclonal goat anti-mNodal | 2 µg/mL, IF<br>2 µg/mL, IHC | R&D Systems, Minneapolis, MN |
| Polyclonal rabbit anti-Nodal (H-110) | 1:500, WB | Santa Cruz Biotechnology, Santa Cruz, CA |
| Polyclonal goat anti-Lefty | 1:500, WB<br>1:50, IF | Santa Cruz Biotechnology, Santa Cruz, CA |
| Monoclonal Mouse anti-Cripto | 1 µg/mL, WB<br>10 µg/mL, IF | R&D Systems, Minneapolis, MN |
| Polyclonal Goat anti-Ki67 | 1:20, IHC | Santa Cruz Biotechnology, Santa Cruz, CA |
| Monoclonal mouse anti-Actin | 1:5000, WB | Chemicon International, Temecula, CA |

Immunofluorescence

Cells were fixed with 4% paraformaldehyde, made permeable with 20 mM Hepes, 0.5% TritonX-100 and blocked with serum-free protein block (DAKO, Carpinteria, Calif.). Primary antibodies were diluted in antibody diluent (DAKO) to the concentrations outlined in SI Table 2, and appropriate fluorochrome-conjugated secondary antibodies were used according to manufacturer recommendations. For certain images, nuclei were stained with DAPI (0.1 mg/mL; Molecular Probes), and images were obtained using confocal microscopy (Zeiss 510 META, Carl Zeiss Inc.).

Immunohistochemistry

Formalin-fixed, paraffin-embedded archival tissue was obtained from patients with primary or metastatic cutaneous melanoma (Loyola University Chicago, Ill.). Immunohistochemical staining was performed on a HNS 710i Automated Immunostainer (Richard-Allan Scientific (RAS), Kalamazoo, Mich.) with the Multi-Species HRP/AEC Detection Systems. Following deparaffinization in xylene, ethanol degradation, and antigen retrieval with citrate buffer, four blocking steps were applied: 0.03% hydrogen peroxide, Avidin and Biotin blocks (Avidin/Biotin blocking kit, Vector Laboratories, Inc., Burlingame, Calif.), and a Serum-Free protein block. Anti-Nodal antibody (20 µg/mL, R&D Systems, Minneapolis, Minn.) was applied for 90 minutes. Slides were rinsed in TBS-T, incubated with biotinylated anti-goat IgG (2 µg/ml, Vector Labs), washed with TBS-T and incubated with the streptavidin peroxidase reagent for 15 minutes. Color was produced with AEC (red) substrate (RAS) and counterstaining with Mayer's hematoxylin. Samples were dehydrated in reagent grade alcohol and cover slipped with permanent mounting medium. Negative control reactions were conducted with ChromPure Goat IgG (Jackson Labs), isotype matched and used at the same concentration as the Nodal antibody. Immunohistochemical staining for Nodal in a breast carcinoma progression TMA (CBL-TMA-029; Creative Biollabs, Port Jefferson Station, N.Y.) was performed as previously described. Topczewska et al., 2006. Tissues from the orthotopic tumor models were formalin-fixed and paraffin-embedded and immunohistochemical staining on this tissue was conducted using a Ki67-specific antibody (Table 2) or ChromPure Goat IgG (Jackson Labs) as previously described. Topczewska et al., 2006. TUNEL assays to measure apoptosis were conducted as per instructions (Upstate).

It should be understood that the foregoing disclosure emphasizes certain specific embodiments of the invention and that all modifications or alternatives equivalent thereto are within the spirit and scope of the invention as set forth in the appended claims. The combination of particular aspects of the various embodiments of the invention is included in the scope of the invention. All patents, patent applications, and other scientific or technical writings referred to anywhere herein are incorporated by reference in their entirety.

We claim:

1. A method of inhibiting Nodal activity in tumor cell growth or aggressive tumors, or both, in a mammal in need thereof comprising intratumorally administering an effective amount of an inhibitor of Nodal activity to the mammal, having at least one tumor cell growth or aggressive tumor, or both, having Nodal activity wherein the inhibitor is Lefty protein and wherein the Nodal activity is inhibited, wherein the Lefty protein is isolated from a microenvironment of human embryonic stem cells ("hESC").

2. The method of claim 1, wherein the Lefty protein is substantially pure.

3. The method of claim 1, wherein the tumor cell growth or aggressive tumor, or both, having Nodal activity is melanoma.

4. The method of claim 1, wherein the tumor cell growth or aggressive tumor, or both, having Nodal activity is breast cancer.

5. The method of claim 1, wherein the Lefty protein inhibits Nodal activity in the tumor cell growth or aggressive tumor, or both, wherein apoptosis is increased, cell proliferation is decreased, vasculogenic mimicry is reduced, or any combination thereof.

* * * * *

SEQUENCE LISTING

<160> NUMBER OF SEQ ID NOS: 22

<210> SEQ ID NO 1
<211> LENGTH: 17
<212> TYPE: DNA
<213> ORGANISM: Artificial
<220> FEATURE:
<223> OTHER INFORMATION: Synthetic

<400> SEQUENCE: 1
ccgcgctggg tgcccag

```
<210> SEQ ID NO 2
<211> LENGTH: 18
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (6)..(7)
<223> OTHER INFORMATION: N can be any nucleotide
<220> FEATURE:
<221> NAME/KEY: misc_feature
<222> LOCATION: (11)..(11)
<223> OTHER INFORMATION: N can be any nucleotide
<220> FEATURE:
<221> NAME/KEY: misc_feature
<222> LOCATION: (15)..(15)
<223> OTHER INFORMATION: N can be any nucleotide

<400> SEQUENCE: 2
ccgcgnnggg ngccncag                                                 18

<210> SEQ ID NO 3
<211> LENGTH: 21
<212> TYPE: DNA
<213> ORGANISM: Artificial
<220> FEATURE:
<223> OTHER INFORMATION: Synthetic

<400> SEQUENCE: 3
ttttagaagg gagtgaattg g                                             21

<210> SEQ ID NO 4
<211> LENGTH: 24
<212> TYPE: DNA
<213> ORGANISM: Artificial
<220> FEATURE:
<223> OTHER INFORMATION: Synthetic

<400> SEQUENCE: 4
aaaaaataaa aacttctaat ctcc                                          24

<210> SEQ ID NO 5
<211> LENGTH: 24
<212> TYPE: DNA
<213> ORGANISM: Artificial
<220> FEATURE:
<223> OTHER INFORMATION: Synthetic

<400> SEQUENCE: 5
agtattttag taaattttt attg                                           24

<210> SEQ ID NO 6
<211> LENGTH: 26
<212> TYPE: DNA
<213> ORGANISM: Artificial
<220> FEATURE:
<223> OTHER INFORMATION: Synthetic

<400> SEQUENCE: 6
attaatatta ctataataat ttaatc                                        26

<210> SEQ ID NO 7
<211> LENGTH: 24
<212> TYPE: DNA
<213> ORGANISM: Artificial
<220> FEATURE:
<223> OTHER INFORMATION: Synthetic
```

```
<400> SEQUENCE: 7
taattttata agattggaga ttag                                          24

<210> SEQ ID NO 8
<211> LENGTH: 24
<212> TYPE: DNA
<213> ORGANISM: Artificial
<220> FEATURE:
<223> OTHER INFORMATION: Synthetic

<400> SEQUENCE: 8
tactaaaacc caaaatataa aaac                                          24

<210> SEQ ID NO 9
<211> LENGTH: 26
<212> TYPE: DNA
<213> ORGANISM: Artificial
<220> FEATURE:
<223> OTHER INFORMATION: Synthetic

<400> SEQUENCE: 9
tttaaattaa aatttagaga taatgg                                        26

<210> SEQ ID NO 10
<211> LENGTH: 21
<212> TYPE: DNA
<213> ORGANISM: Artificial
<220> FEATURE:
<223> OTHER INFORMATION: Synthetic

<400> SEQUENCE: 10
actttcaaac ctaaccaacc c                                             21

<210> SEQ ID NO 11
<211> LENGTH: 23
<212> TYPE: DNA
<213> ORGANISM: Artificial
<220> FEATURE:
<223> OTHER INFORMATION: Synthetic

<400> SEQUENCE: 11 tagttttaa ggtttagggt gtg                                            23

<210> SEQ ID NO 12
<211> LENGTH: 21
<212> TYPE: DNA
<213> ORGANISM: Artificial
<220> FEATURE:
<223> OTHER INFORMATION: Synthetic

<400> SEQUENCE: 12
tactaaccct actcttatcc c                                             21

<210> SEQ ID NO 13
<211> LENGTH: 23
<212> TYPE: DNA
<213> ORGANISM: Artificial
<220> FEATURE:
<223> OTHER INFORMATION: Synthetic

<400> SEQUENCE: 13
agttttagtt ggggttttt aag                                            23

<210> SEQ ID NO 14
<211> LENGTH: 22
<212> TYPE: DNA
```

-continued

<213> ORGANISM: Artificial
<220> FEATURE:
<223> OTHER INFORMATION: Synthetic

<400> SEQUENCE: 14
ttaaaaacca acacacacct ac                                    22

<210> SEQ ID NO 15
<211> LENGTH: 23
<212> TYPE: DNA
<213> ORGANISM: Artificial
<220> FEATURE:
<223> OTHER INFORMATION: Synthetic

<400> SEQUENCE: 15 tagttttga ggtttagggt gtg                                    23

<210> SEQ ID NO 16
<211> LENGTH: 20
<212> TYPE: DNA
<213> ORGANISM: Artificial
<220> FEATURE:
<223> OTHER INFORMATION: Synthetic

<400> SEQUENCE: 16
tatctcctaa cctaactacc                                       20

<210> SEQ ID NO 17
<211> LENGTH: 23
<212> TYPE: DNA
<213> ORGANISM: Artificial
<220> FEATURE:
<223> OTHER INFORMATION: Synthetic

<400> SEQUENCE: 17
agttttagtt ggggtttttt aag                                   23

<210> SEQ ID NO 18
<211> LENGTH: 21
<212> TYPE: DNA
<213> ORGANISM: Artificial
<220> FEATURE:
<223> OTHER INFORMATION: Synthetic

<400> SEQUENCE: 18
ctcaataacc ctaccatcct c                                     21

<210> SEQ ID NO 19
<211> LENGTH: 25
<212> TYPE: DNA
<213> ORGANISM: Artificial
<220> FEATURE:
<223> OTHER INFORMATION: Synthetic

<400> SEQUENCE: 19
cctcttacct cagttacaat ttata                                 25

<210> SEQ ID NO 20
<211> LENGTH: 25
<212> TYPE: DNA
<213> ORGANISM: Artificial
<220> FEATURE:
<223> OTHER INFORMATION: Synthetic

<400> SEQUENCE: 20
aagcagcacc tccagcccctt atatc                                25

```
<210> SEQ ID NO 21
<211> LENGTH: 21
<212> TYPE: DNA
<213> ORGANISM: Artificial
<220> FEATURE:
<223> OTHER INFORMATION: Synthetic

<400> SEQUENCE: 21
gccacatggt gctgccctgg g                                                   21

<210> SEQ ID NO 22
<211> LENGTH: 23
<212> TYPE: DNA
<213> ORGANISM: Artificial
<220> FEATURE:
<223> OTHER INFORMATION: Synthetic

<400> SEQUENCE: 22
ctgcatggtg ctgccctgga gga                                                 23
```